(12) United States Patent
Schryver

(10) Patent No.: US 12,290,067 B2
(45) Date of Patent: May 6, 2025

(54) MULTI-FUNCTIONAL CRYOGENIC STORAGE VESSEL

(71) Applicant: ASTERO BIO CORPORATION, Pleasanton, CA (US)

(72) Inventor: Brian Schryver, Redwood City, CA (US)

(73) Assignee: BIOLIFE SOLUTIONS, INC., Bothell, WA (US)

( * ) Notice: Subject to any disclaimer, the term of this patent is extended or adjusted under 35 U.S.C. 154(b) by 1185 days.

(21) Appl. No.: 17/049,300

(22) PCT Filed: Apr. 22, 2019

(86) PCT No.: PCT/US2019/028566
§ 371 (c)(1),
(2) Date: Oct. 20, 2020

(87) PCT Pub. No.: WO2019/204821
PCT Pub. Date: Oct. 24, 2019

(65) Prior Publication Data
US 2021/0244019 A1    Aug. 12, 2021

Related U.S. Application Data

(60) Provisional application No. 62/660,722, filed on Apr. 20, 2018.

(51) Int. Cl.
*A01N 1/02* (2006.01)
*B65B 3/00* (2006.01)
*B65D 1/02* (2006.01)

(52) U.S. Cl.
CPC ......... *A01N 1/0268* (2013.01); *A01N 1/0273* (2013.01); *B65B 3/003* (2013.01); *B65D 1/0223* (2013.01)

(58) Field of Classification Search
CPC .... A01N 1/0268; A01N 1/0273; B65B 3/003; B65D 1/0223
(Continued)

(56) References Cited

U.S. PATENT DOCUMENTS

| 4,482,585 A | 11/1984 | Ohodaira et al. |
| 5,964,096 A | 10/1999 | Watson et al. |

(Continued)

FOREIGN PATENT DOCUMENTS

| EP | 0098312 A1 | 1/1984 |
| JP | 2013174512 A | 9/2013 |

(Continued)

OTHER PUBLICATIONS

EP Search Report for International Application PCT/US2019028566—EP Application 19789122, dated Dec. 23, 2021.

(Continued)

*Primary Examiner* — Jill A Warden
*Assistant Examiner* — Jacqueline Brazin
(74) *Attorney, Agent, or Firm* — Brown & Michaels, PC

(57) ABSTRACT

Systems and devices with enhanced stability to kinetic impact for the containment of cryogenically preserved material. A device comprising a vessel with increased surface to volume ratio when compared to cylindrical vessels of like capacity, and further comprising a material that remains resistant to shock and impact at cryogenic temperatures while providing a continuous barrier of a single material surrounding the vessel contents. The device further comprising a design that may be readily modified to include internalized sensors, enhanced interfacing to external instruments, provide optimized thaw rate, and post-thawing sample processing capabilities.

57 Claims, 23 Drawing Sheets

(58) Field of Classification Search
USPC .................................................. 435/283.1
See application file for complete search history.

(56) References Cited

U.S. PATENT DOCUMENTS

| | | |
|---|---|---|
| 6,517,526 B1 | 2/2003 | Tamari |
| 8,678,225 B2 | 3/2014 | Janssen et al. |
| 2003/0215369 A1 | 11/2003 | Eggers et al. |
| 2004/0156756 A1* | 8/2004 | Brink .................. B01J 19/0046 422/130 |
| 2007/0240432 A1* | 10/2007 | Voute ...................... A61J 1/165 62/66 |
| 2008/0261288 A1* | 10/2008 | Gonda ................... C12M 25/14 435/174 |
| 2010/0072216 A1 | 3/2010 | Voute et al. |
| 2015/0259119 A1 | 9/2015 | Duan-Arnold et al. |
| 2015/0305324 A1 | 10/2015 | Ilyin et al. |
| 2017/0259260 A1 | 9/2017 | Raes et al. |
| 2020/0405957 A1* | 12/2020 | Le Baccon ............ H04N 23/55 |

FOREIGN PATENT DOCUMENTS

| | | | |
|---|---|---|---|
| JP | 2015042212 | * | 3/2015 |
| JP | 2015042212 A | | 3/2015 |
| WO | 1997049959 A2 | | 12/1997 |
| WO | WO-2012165630 A1 * | 12/2012 | ............. B65D 53/08 |

OTHER PUBLICATIONS

International Search Report for PCT/US2019/028566 dated Jul. 30, 2019.

* cited by examiner

MULTI-FUNCTIONAL CRYOGENIC STORAGE VESSEL

FIELD OF THE INVENTION

This invention relates to vessel devices that securely contain frozen cell suspensions at cryogenic temperatures while also providing enhanced protection from impact, shock, and acceleration damage. The invention also pertains to cryogenic storage vessels having sensors and communication interfaces. In addition, the invention relates to cryogenic storage vessels that facilitate the interaction of the vessels with other devices during storage, transport, the thawing process, and after the thawing process. Lastly, the invention relates to cryogenic storage vessels configured to accommodate fluidic procedures and cell processing in a container stored within the vessel and prior to removal of the vessel contents after thawing.

BACKGROUND OF THE INVENTION

The field of live-cell based pharmacology has been well established and will continue to expand and advance further in the future. Many of the cell-based therapeutics require cell populations to be expanded to greater number following a variety of processing steps. Once the populations have been expanded there often comes a need to store the cells for an extended time period. For example, there may be a need to administer the cells to a recipient over a protracted interval, or the therapeutic may be intended for administration to a group of individuals that are not yet identified, or there may be a need to simply hold a cell population indefinitely as a future resource or reference sample. Another exemplary reason may be simply that the recipient is at a remote location and the transport interval would be too great. Cells, however, are living and dynamic. In culture they continue to grow and require a fresh nutrient source and a means for removal of waste, therefore simple shelf storage for these organisms is not possible. There is, however, a means to metabolically stop time for cell suspensions that involves suspending the cells in a cryogenic storage fluid and freezing the cells at a defined rate of temperature loss. When the suspension has solidified and decreased in temperature sufficiently, the frozen cells may be stored indefinitely provided that the temperature of the frozen mass is held below a defined maximum value. Cell suspensions that are cryogenically preserved in this manner are typically stored in vacuum-insulated storage vessels that use liquid nitrogen as a refrigerant and therefore maintain the frozen cells in a typical temperature range of −196 C to −150 C.

The cryogenic storage vessels that are currently commercially available primarily fall into two groups. The first group includes rigid-wall vessels typically constructed from molded resin materials. Through selected material properties and wall thickness specifications, these rigid vessels have a toughness at cryogenic temperatures sufficient to withstand forces and impact shocks. The geometric configuration of rigid vessels is predominantly cylindrical with a narrowing at the access port. To provide a means of filling and dispensing contents, the port opening is typically blocked with a rubber-like material septum plug that may be readily penetrated by hypodermic-style needles or specifically-designed filling needles. Due to the differential in expansion coefficients of the vial resin material and the septum material, in addition to the difficulty in bonding the rubber material to the resin material with a joint that will remain intact at cryogenic temperatures, rubber septum plugs are frequently secured to the resin vial rim by means of a secondary retainer of aluminum or plastic. Although retainers are effective in preventing separation and may add additional clamping force, the hardening and shrinkage of the rubber material at temperatures below −50 C may make the vessel seals unreliable at cryogenic temperatures, thereby imposing concerns regarding contamination potential, release of live materials to the environment, and explosive ejection of the rubber plug following liquid nitrogen aspiration.

Additional challenges imposed by rigid vessels derive from difficulties in interfacing to solid heating blocks due to the curvature of the vials. Moreover, with cylindrical vessels, the surface to volume ratio decreases with increased volumetric capacity as the radial dimension is increased, and as such, the rate of heat influx during the thawing process becomes a limitation resulting in extended thawing intervals. In a rigid-wall vessel during the thawing process, with the thermal energy being introduced into the vessel at the inner wall boundary, phase conversion begins at the inner wall and progresses to axial center of the cylindrical frozen mass. As such, during the thawing process, a thermal gradient will be introduced thereby subjecting cells within the gradient region to protracted intervals at temperatures that may damage the cells.

The second group of storage vessels includes flexible containers, such as the flexible cryostorage bag format. These types of storage vessels offer potential advantages over rigid-wall vessels while also introducing a vulnerability to kinetic damage when compared to rigid vessels. Cryostorage bags are typically not filled to capacity, but rather are filled to a capacity that will allow a typical thickness limit of approximately 1 cm. The limited thickness of the frozen mass in combination with the large surface area of the bag allows greater control of cooling rate during the freezing process as well as a significantly reduced interval during the thawing process compared to rigid vessels for a comparable load volume. In addition, the flexible property of the bag material allows convective distribution of thermal energy during the thawing process by means of vessel wall movement and mixing of the contents.

A major vulnerability of the cryostorage bag is the susceptibility to breakage at low temperatures. Cryostorage bags are typically constructed from two laminations of a sheet polymer material that are joined on the boundary edges with a fusion heat seal. The stiffness of the polymer sheet material increases to brittleness as the temperature of the material is reduced to cryogenic temperatures. As a result, an impact to the frozen bag, particularly along the boundary edge may result in crack formation or fracture of the bag material. Cryostorage bag contents are typically introduced and withdrawn through port assemblies that are fusion bonded between the major lamination layers along a seam edge. Protrusion of the port assemblies impose a potential for impact or torsion forces to concentrate stresses leading to failure at the port to bag joint. Although the ports provide a continuous material seal that is more reliable than those constructed from multiple interfaced materials, as the seals are typically penetrated using a tube needle or spike to remove the vessel contents, the potential hazard of accidently perforating the bag wall is a concern, unless specific protective design features are incorporated.

An additional drawback of cryostorage bags derives from the aspect that as liquid contents are withdrawn, the inner walls of the bag are positioned in close proximity and as a result, a surface tension of aqueous solutions acts to retain liquid inside the bag, even under the assistance of gravitation. Consequently, an unrecoverable dead volume loss is imposed unless extraordinary measures are applied, such as roll-wringing of the bag.

Accordingly, although various methods and devices currently exist for the storage of sensitive frozen materials, challenges remain. The devices and methods of the present invention address and meet these needs.

SUMMARY OF THE INVENTION

The present invention relates generally to devices that provide for the containment of liquid samples that are subsequently frozen and stored for the purpose of cryopreservation. In the first aspect, the present invention is directed to cryogenic storage vessels that provide protection from impact, shock, and acceleration or damage due to applied mechanical forces, wherein, upon filling and sealing the storage vessel, the storage vessel comprises a complete and continuous interior surface comprised of a single material that is joined in a seam closed by a fusion bond. In some instances, the vessels are constructed from cryogenic-compatible materials that provide toughness, reduced embrittlement, maximize flexibility and resistance to shock and stress fracture at cryogenic temperatures, while being sufficiently flexible and pliant at ambient and aqueous solution freezing temperatures to allow limited adjustment to the volumetric capacity by compressive mechanical forces or by expansion pressure of the aqueous contents upon solidification. In some instances, the invention provides for cryogenic storage vessels that are semi-rigid such that the dimensions of the vessel do not collapse in the gravitational field, thereby preventing inner surface tensions that result in retention of liquids contained therein upon emptying.

Some instances of the invention provide varied dimension to control a surface-to-volume ratio of the vessel. For example, in some instances one dimension of the vessel is minimized while the remaining two dimensions are adjusted to optimize the area of flat surfaces on two major parallel planes, thereby controlling the surface to volume ratio such that contact of the larger planar surfaces with an external planar heat sink or heat source provides a rapid transition time between cryogenic temperatures and the melting temperature of the vessel contents. To allow for expansion of aqueous contents during freezing and to provide for the option of minimizing air void while filling the vessels, some embodiments of the invention provide one or more rim expansion curvatures that allow an increase in a separation distance of at least two major vessel surfaces, while maintaining a parallel planar orientation of the major vessel surfaces. In some instances, a first dimension of the vessel is made smaller than the remaining two dimensions of the vessel, wherein the two major dimensions control an area of a major surface on each vessel shell part, where a third dimension controls a distance between the major surface of each shell part when the vessel is assembled. In some embodiments, a ratio between a first dimension and a combined dimension of a second dimension and a third dimension is from 1:1 to 4:1. In some embodiments, a ratio between a first dimension and a third dimension is from 1:1 to 30:1. In some embodiments, a ratio between a first dimension and a third dimension is from 2:1 to 20:1. In some embodiments, a vessel of the present invention comprises an area determined by a first dimension and a second dimension, wherein the area is from 3 $cm^2$ to 300 $cm^2$, or from 300 $cm^2$ to 1000 $cm^2$.

In some instances, a storage vessel comprises two halves that substantially mirror one another, each comprising a nominally rectangular major surface with rounded corners, the perimeter of each major surface being joined with a swept profile rim, and the opposite or un-joined edge of the swept profile rim being joined with an outwardly directed flange, wherein the two vessel parts are configured to be joined in a seam at a mirror plane of the two halves, with a fused flange seal. In some embodiments, a flange of the present invention comprises a width greater than 1 mm. In some instances, the vessel comprises a first half or part with a nominally rectangular major surface with rounded corners, a perimeter of the major surface being joined with a swept profile rim, and the opposite or un-joined edge of the swept profile rim being joined with an outwardly directed flange, the outwardly directed flange being joined with a planar surface of a second half or part, wherein joining the first and second parts by means of a heat welded joint at the flange surface closes an interior of the vessel.

In some instances, the invention provides a vessel wherein one or more halves or parts of the vessel comprises a cavity having a nonlinear swept rim wall profile configured to extend and/or contract to allow for adjustment of an interior volume of the cavity, wherein the nonlinear swept rim wall profile is flared outwardly from a major surface of the vessel part toward a rim flange of the cavity.

In some instances, the fused flanges and the rim profile of the vessel may engage with a bumper frame configured to protect the vessel during a lifecycle of the product, including filling, freezing, transport, storage, and thawing procedures.

In some instances, a vessels comprises one or more access ports that are located away from one or more midline seams, offset seams, or minor surfaces of the vessel, thereby protecting the access ports from impact, shock, or unintentional mechanical distortions or stresses. In some instances, the access ports comprise an integrated port, wherein the integrated port is an uninterrupted continuation of the vessel wall material, thereby providing an access port seal that is not reliant upon bonded seams of either like or unlike materials. In some instances, no additional construction of access ports is necessary beyond a molding of specific depressions or curvature in the vessel surface, while in other instances, access to the contents of the vessel may be achieved by directly penetrating a wall surface of the vessel. In some instances, a recess that serves as an access port in a surface of the vessel may be occluded by a removable membrane, wherein following sterilization of the finished vessel, the membrane maintains a sterile state of the access port until the membrane is removed.

In a second aspect, the vessel comprises a first half or part having a nominally rectangular major surface with rounded corners, a perimeter of the major surface being joined with a swept profile rim, and the opposite or un-joined edge of the swept rim being joined with an outwardly directed flange, the first part being joined at a surface plane of the flange with a second half or part comprising a planar surface, wherein joining the first and second parts, by means of a heat welded joint, closes an interior of the vessel. In some instances, the vessel further comprises a driver element comprising a flat, thin sheet form of ferritic material that is laminated between two layers of material having identical or similar properties to the material of the first and second parts of the vessel, wherein when the driver element is positioned in the interior of the vessel, the driver element biases solid contents of the vessel to a specific region of the vessel interior when exposed to an external magnetic field. In some instances, a planar wall of the vessel comprises electronic circuitry having circuit leads that terminate at one or more locations on an edge of the planar wall. In some instances, the vessel comprises electronic circuitry having circuit leads that terminate at one or more locations on an outside surface of the planar wall. In some instances, at least one of the electronic circuits comprises a sensor by which one or more parameters of the contents of the vessel is measured and/or monitored, such the temperature, pH, alkalinity, or oxygen level.

In a third aspect of the invention, a vessel is provided that comprises an external wall constructed from two opposing parts joined at a median plane seam, and where one dimension of the vessel is smaller than the remaining two dimension such that the vessel has two large planar surfaces joined by a swept rim wall that terminates in a flange seam joined in a heat weld, and additional seams that form a seal division of the vessel and that also join with swept rims through the interior portion of the vessel such that the vessel is divided into two or more compartments that are completely isolated from one another except at specific locations where through-ducts may allow communication between the two separate enclosed compartments or volumes. In some instances, one or more through-ducts are normally occluded by a valve mechanism. In some instances, a valve opens when the vessel is subjected to sufficient centrifugal force aligned with a specific vector. In some instances, a method for using a vessel of the present invention comprising steps for filling a first cavity of a vessel with a cell suspension containing a cryopreservation fluid, and filling a second cavity of the vessel with an exchange medium, wherein upon thawing the cryopreservative medium, cells are transferred from the first cavity and into the second cavity, whereby the cryopreservative medium is substantially diluted or absent. In some instances, the cells in the first cavity of the vessel are promoted through one of the ducts by a centrifugal force at the same time that the same centrifugal force promotes the opening of the duct communicating with the first and second cavity, thereby allowing passage of the cells into the second cavity. In some instances, a second communication duct joining the first cavity and the second cavity is occluded by a valve that is located proximal to the axis of rotation at which an angular displacement creates a centrifugal force upon the vessel. At a sufficient level of relative centrifugal force, the valve in the second communication duct is opened, and being proximal to the remainder of the vessel, and as liquid contents of the vessel will be displaced to the distal portion of the vessel, the open second communication duct valve allows gas pressure to equilibrate between the two vessel chambers, thereby eliminating any pressure differential between the two chambers when the centrifugal force is absent.

In a fourth aspect, the present invention includes methods for the use of the vessels described in the first through third aspect above. Some aspects of the methodology apply to the loading and sealing sequence that may be used to introduce liquids into the vessels in a sterile manner and to subsequently close the vessels in a fusion seal. Other aspects of the methodology apply to the sequence of steps that may be applied for the sterile extraction of liquid contents from the vessels.

These aspects, embodiments, and advantages of the invention are described in greater detail in the attached drawings and in the following detailed description.

DETAILED DESCRIPTION OF THE INVENTION

Figure 1:
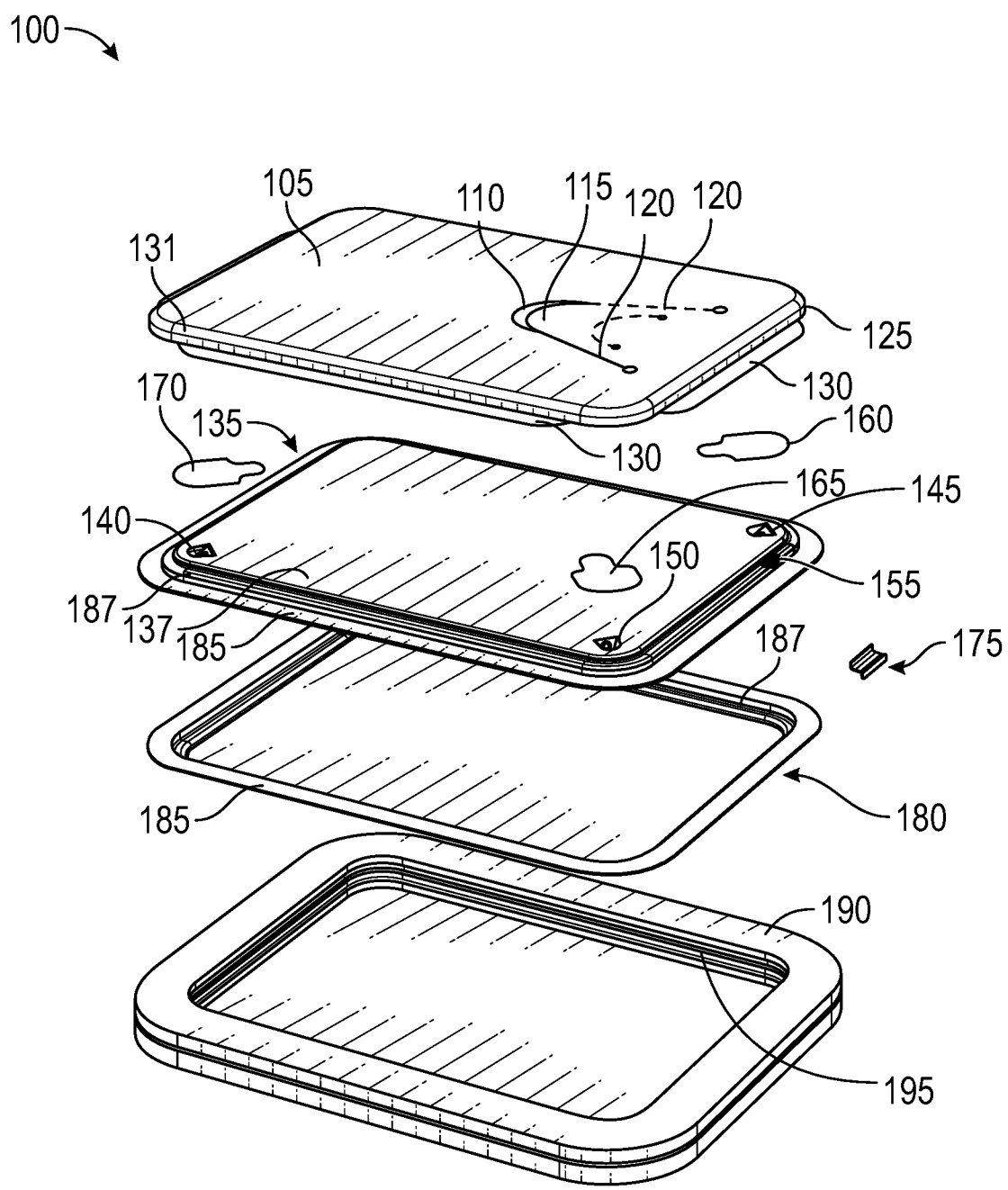
FIG. 1 shows an exploded view depicting the key elements of a vessel assembly is shown, in accordance with a representative embodiment of the present invention.

The present invention provides storage vessels and storage systems for cryogenically preserved cell suspensions that satisfy a number of properties and functionalities that are not offered in vessels that are currently available. In some embodiments, the vessels of the present invention provide a means of containment of a liquid and/or aqueous solution, for example, a solution, a composition, a formulation, a particulate suspension, a viral suspension, a cellular suspension, and a multicellular organism suspension. In some embodiments, the liquid is contained within a vessel by a barrier of a singular material wherein various parts comprising the vessel are joined by fusion bonds of the singular material, and as such are not vulnerable to separation of parts and failure of bonds under the stresses imposed by exposure to low and cryogenic temperatures. In some embodiments, the singular material has the properties of retaining toughness, flexibility, and resistance to fracture at cryogenic temperatures while offering self-supporting geometric rigidity and selective penetrability at ambient temperatures. In some embodiments, the singular material is a thermoplastic polymer or polymer blend that may be vacuum formed from sheet material thereby providing an inexpensive means of construction allowed by low cost vacuum molding and heat fusion bonding, in addition to allowing for low cost heat forming of essential localized features in the parts prior to final assembly. In other embodiments the vessel may be produced from the same material using an injection molding system. In some embodiments, the installation and removal of vessel contents may be accomplished by direct penetration of the vessel wall. In some embodiments, perforations of the vessel wall during the filling process may be sealed by means of a plug that is constructed from the same material as the vessel wall and which is sealed in place by heat fusion bonding of the plug to the vessel wall. In some embodiments, specialized filling ports are provided which form a continuum with the vessel wall, wherein the specialized filling ports may be used to install vessel contents and be subsequently collapse sealed with a heat fusion bond at or near to the port vessel wall junction with concurrent or subsequent removal of the portion of the port structure that is distal to the heat fusion bond or seal. In some embodiments, specialized port structures are molded into the surface of the vessel, wherein these ports are configured to facilitate the installation or removal of vessel contents by vessel wall penetration. In some embodiments, the specialized port structures or port bays are recessed from the main surface of the vessel such that no part of the port structure protrudes above the main surfaces of the vessel. In some embodiments, the recessed port structures or bays are occluded by removable hermetic seals that maintain the sterility of the recessed port bay volume until removed. In some embodiments, the storage vessels comprise an enclosure of the same material that form a continuous wall barrier at all points that come in contact with the vessel contents. In some embodiments, the vessel is constructed from two parts, while in other embodiments the vessels are constructed from more than two parts. In some embodiments, the vessel walls are constructed from two shell parts that each comprise a rim flange, wherein the two shell parts are joined at their respective rim flanges via a heat fusion bond. In some embodiments, the rim flange comprises one surface that is entirely planar. In some embodiments, at least one rim flange deviates from a planar configuration at one or more locations. In some embodiments, the two shell parts of the vessel are symmetric with respect to a plane located along the fusion bond of the two shell parts. In some embodiments, the two shell parts forming the vessel shell are asymmetric. In some embodiments, one of the vessel shell parts or halves is a planar surface.

In some of the embodiments, the dimension of the vessel that is perpendicular to the heat fused flange joint is shorter than the other two dimensions such that the vessel is a nominally flattened and rectangular shape. In some embodiments, the flattened and rectangular shape comprises two major planar and parallel surfaces on opposite sides of the flange joint. In some of the embodiments, the vessel wall that is interposed between the planar surfaces and the respective flanges on the same part comprises a swept rim profile. In some embodiments, the swept rim profile comprises a curvature that allows the dimension between the flange and the planar surface to be decreased or increased at both ambient and lower temperatures, wherein a phase change of the aqueous content of the vessels would occur at the lower temperatures.

In some embodiments, molded port bays are located on the surface of the vessel such that the port bays do not occupy any portion of the heat fusion bond, do not participate in the heat fusion bond, or are not interposed structures within the heat fusion bond that joins the two shell parts of the vessel exterior once the vessel contents have been installed. In some embodiments, the port bays are confined to one of the two shell parts that form the vessel. In some embodiments, port bays may be located on one or more of the shell parts. In some embodiments, none of the vessel shell parts comprise port bays. In some embodiments, port bays may be molded into the rim wall of the vessel. In some embodiments, selected regions of the port bay wall may be reduced in thickness to specific dimensions, such as by local molding and/or thermal forming methods, wherein penetration of the vessel wall may be facilitated for installation and removal of vessel contents. In some embodiments, selected regions of the port bay may be thermally modified to form depressions or well shapes within the port bay wall. In some embodiments, a depression comprises a single radially-symmetric wall. In some embodiments, a depression comprises at least two walls. In some embodiments, the at least two walls comprise a subregion having a thickness less than a wall thickness of a remainder of the at least two walls. In some embodiments, the depression is located on a corner surface of at least one of the first and second major surfaces of a first or second shell of a vessel of the present invention. In some embodiments, the depression in located on a swept rim of a vessel of the present invention.

In some embodiments, the flange rim comprises an extension at one or more locations on or along the flange, wherein the extension forms a conduit that terminates in a vessel access port. In some embodiments, the access port comprises a rubber material septum plug or plug assembly, while in other embodiments the access port is molded into the rim wall, while in other embodiments an extension or a third vessel surface that is thermally fused with the rim wall and flange forms the access port. At the completion of the installation of the vessel contents, the rim and flange extension may be collapsed and thermally fused to seal the conduit, after which a distal portion of the extension beyond the seal may be removed by severance at the seal boundary.

In some embodiments, one of the shell parts of the vessel comprises a flange, a planar wall that is offset and parallel to the flange, and a swept rim interposed and continuous between the planar wall and the flange, wherein the swept rim comprises curvature that allow the dimension between the flange and the planar surface to be reduced or extended by some amount, and wherein the swept rim profile continuously flares from the planar surface junction to the flange junction such that solidified contents molded within the interior cavity of the shell part may be removed on a vector that is perpendicular to the planar wall without interference by the vessel shell part. In some embodiments, the described vessel shell part is closed by thermal bonding (such as a heat weld) of the flange rim to a planar part forming a vessel with two flat and parallel surfaces wherein one flat surface has a greater area than the other flat surface and forms a closure on the shell part.

Some embodiments comprise interior volumes, shapes, and features structured so that when the vessel contains a solidified aqueous solution, and a heater surface is placed in contact with an exterior of the larger planar surface of vessel, means for driving the solidified mass to contact the interior surface of the larger area planar vessel wall results in a rapid phase change of the solid aqueous mass. In some embodiments, a planar sweeper or driver card component is installed in the interior of the described vessel. In some embodiments, a driver card comprises a thin sheet structure comprising a material upon which a displacement force is imposed when the material is placed in a magnetic field, which is completely laminated within two layers of a material from which the vessel wall is constructed. In some embodiments, the thin sheet structure material is a ferritic material. In some embodiments, the ferritic material is a stainless ferritic steel.

In some embodiments, one or more shell parts comprise a lamination of material. In some embodiments, one or more shell parts comprise multiple laminations of material. In some embodiments, electronic circuitry is embedded within or inserted between the layer laminations. In some embodiments, the electronic circuits held between shell lamination layers may further comprise electronic sensors circuitry. In some embodiments, data that is representative of the status of a physical property of the vessel contents may be collected by electronic circuits held between the lamination layers of the vessel shell part. In some embodiments, the electronic circuits comprise data linkage structures exposed to the external environment such that by contacting the exposed circuits, external instrumentation or machinery may exchange electronic signals with the circuits contained between the shell part laminations.

In some embodiments, a vessel of the invention is subdivided into two or more separate chambers. In some embodiments, the two or more separate chambers are interconnected. In some embodiments, the two or more separate chambers are interconnected by a pathway comprising a passageway, a conduit, a valve, a gate, an aperture, a lumen, a tube, a channel, a tunnel, a through-hole, or other similarly compatible structure. In some embodiments, the separate chambers are separated by swept rim boundaries that adjoin with flat tracts on one vessel shell part, wherein like areas or adjoining areas of the two shell parts are fused together, such as by heat fusion. In some embodiments, the vessel containment volume is formed by cavities on both shell parts. In some embodiments, the vessel containment volume is formed by one or more cavities formed on a single shell part, wherein the one or more cavities are closed by a planar shell surface on the second or joining shell part. In some embodiment, chamber separations are interrupted by conduits that connect the otherwise separated chambers. In some embodiments, the conduit connections are selectively open or blocked by gate or valve mechanisms to perform specific functions. In some embodiments, the gate or valve mechanisms are actuated by influences that are external to the sealed shell walls of the vessel. In some embodiments, the gate or valve actuation influences include electrical fields, magnetic fields, of centrifugal forces. In some embodiment, the two or more chambers are filled with different fluids. In some embodiments, suspended particles may be promoted to move from one chamber to the next by centrifugal force, magnetic fields, or electrical fields. In some methods, cells may be present in suspension in one fluid in a chamber of a vessel and subsequently transferred to another fluid in another chamber the vessel, with minimal mixing of the two fluids. In some methods, cells that are suspended in a cryoprotective medium in one chamber of the vessel may be transferred to another chamber of the vessel containing recovery medium, or injection medium, under the influence of a centrifugal force, with minimal mixing of the two media. In some methods, the cells are concentrated during the transfer process, while in other methods, the cells are diluted during the transfer process.

Some of the features of the invention are generally described in FIGS. 1-16C which are provided for the purpose of illustrating the practice of some embodiments of the invention and which do not constitute limitations of the scope thereof.

Now referring to FIG. 1, an exploded view of a shell storage or containment vessel of the present invention is shown. In some embodiments, a containment vessel is provided comprising a first or upper or top shell part 135 and a second or lower or bottom shell part 180 each of which comprises a major planar surface 137 (representative for both parts) and a flange 185 that are both connected around the entire perimeter by a swept rim 187. The profile of the swept rim provides additional functionality and will be described in further detail in subsequent figures. The two vessel shell parts 135, 180 are joined at the faces of the flanged rims 185 in a heat weld, such that the interior of the resulting vessel volume is completely isolated from the exterior at all surfaces and points.

In some embodiments, the vessel shell parts comprise a material that retains the properties of toughness, flexibility, and resistance to fracture at cryogenic temperatures as well as at ambient temperatures. In some embodiments, the material is a copolyester polymer. In some embodiments, the copolyester polymer is a Tritan™ copolyester, while in other embodiments the copolyester polymer is Tritan™ copolyester MP100 sold by Eastman Chemical Co. In some embodiments, the shell parts may be formed from sheet material by a process of vacuum molding. In other embodiments, the shell parts may be formed by an injection molding process. In some embodiments, the thermoplastic shell part materials may be joined by a thermal fusion bond. In other embodiments, the welding process may be ultrasonic welding, while in other embodiments, the welding process may be laser welding.

In some embodiments, the flange rim 185 of the vessel is contained within a slot recess 195 (described in greater detail in subsequent cross-section figures) that is contained within a bumper frame part 190 that may surround part of, or the entirety of, the vessel perimeter. In some embodiments, the bumper is installed during any combination of any phases of the use cycle of the shell vessel, including the preloading, loading, freezing, storage, transport, and thawing phases for the protection of the flange joint and rim perimeter of the vessel. In some embodiments, the bumper frame is constructed from bonded laminations of a felt material while in other embodiments, the bumper is constructed from a foam material. In some embodiments, the bumper felt material is a polypropylene felt. In some embodiments, the felt material laminations are bonded by stitching, while in other embodiments, the felt laminations are bonded by thermal welds or by adhesive bonds.

In some embodiments, the major planar surface on the top shell 135 comprises molded therein one or more depressed access ports or port bays 145, 140, 150. The port bays comprise features that will be described in greater detail in subsequent figures, however in general each port bay or bay comprises a surface angled with respect to the major plane surface 135 with each angled surface further comprising a molded target feature. In some embodiments, the molded target feature marks the location where the vessel wall thickness has been either unmodified or reduced in thickness so as to reduce the force necessary to penetrate the material with a tubular needle or access device. In other embodiments, the molded target feature comprises depressions or tapered conical entryways so as to facilitate engagement with matched taper or threaded adapters. In some embodiments, the direction of the port bay angled surface is controlled so as to provide functional directionality to the feature, particularly with regard to the angle of tilt in the gravitation field that will facilitate the use of or optimize the outcome of various steps and methods applied for the use of the invention. As such, in some embodiments, some port bays have assigned functionality and nomenclature. For example, the port 150 is angled and directed such when the corner on which the port is positioned is elevated above the remaining corners of the vessel, the port may be optimally used for filling the vessel and as such may be referred to as the "fill port". Likewise, the port 140 may be elevated above all other corners of the vessel to provide a gas venting of the internal volume of the vessel when the port is punctured and may be referred to as the "vent port", while port 145 when held at a level lower than the other ports may be optimally used for withdrawing the vessel contents and as such may be referred to as the "extraction port". While the example embodiment shown in FIG. 1 presents port bays in defined positions, in specific numbers, and are described as having specific functions, the example is not intended to be limiting, and indeed the number of and the position of the port bays and the intended functional use of any port bay may be different in other embodiments, and the unlimited configuration options provided by the described port access is one of the key benefits of the port bay design. In some embodiments, port bays may be exclusively limited to one of the two shell parts, while in other embodiments, port bays may be present on both shell parts, or installed on additional parts conjoined with the two shell parts. For embodiments where the port bays are recessed below the main surface of the shell plane, an occlusion seal 160, 165, 170 may be non-permanently bonded to the shell surface to isolate and seal the port bay recess. In some embodiments, the seal comprises an attached tab that is not bonded or weakly bonded to the surface of the shell so that the tab may be use to remove the seal from the port. In some embodiments, the seal is airtight and capable of maintaining the sterility of the port bay following the sterilization of the entire vessel assembly. In some embodiments, the seal is a laminated polymer and metal foil seal.

One familiar with the art and practice of using cryogenic storage vessels will recognize that all currently available vessels are associated with a difficulty in withdrawing the entire contents of the vessel, often necessarily forcing the operator to abandon a portion of the contents in the vessel. Often this difficulty may be imposed in part by the properties of the beveled hypodermic-style needle used to withdraw the vessel contents as the bevel needle tip will begin to aspirate the gas content of the vessel, thereby breaking the vacuum induced pressure differential used to withdraw the contents. In some embodiments, the present invention provides a port 155 located at a position on the rim wall, thereby permitting the bevel portion of a needle to contact the vessel interior corner seam with an exact acute angle of the needle tube bevel (typically 12 degrees, for example), thereby facilitating the entire contents of the vessel to be removed by vacuum aspiration. In future reference, this port may be referred to as the "last drop port". As with the previously described ports, the last drop port 155 may be occluded by a seal 175 until specific access to the port is required.

As the seals 160, 165, 170, 175 typically comprise thin material which may, in some embodiments, be vulnerable to puncture, during storage and transporting operations, a protective cover overlay 105 that is molded to match some dimensions and contours of the shell vessel may, in some embodiments, be placed over the shell surface to protect the port bay seals. In one embodiment, the protective cover 105 is held in contact with the vessel shell assembly by flange extensions 130 that are attached to the cover 105 along a portion of, or the entire length of, the edge of the cover rim 131. In some embodiments, the cover rim flanges 130 are contained within the slot 195 of the felt bumper 190 coincident to the rim flange 185 of the upper vessel shell 135. In some embodiments, the absence of the cover flange 130 at the corners 125 of the cover allow the flanges 130 to flex and become disengaged from the felt bumper slot 195 by temporarily displacing the pliant felt of the bumper 190 when an upward force is applied to the cover, and by this means the cover 105 may be disengaged from the vessel and bumper assembly. In some embodiments, the cover 105 is held in place by only two cover flanges 130 while in other embodiments, more than two cover flanges are provided. To facilitate the removal of the cover from the shell vessel and bumper assembly, in some embodiments, a pull-tab feature 115 is provided as a partial cut out in the major plane of the cover piece 105. In some embodiments, a slot cutout 110 is provided whereby the tab may be raised and pulled thereby breaking two lines of perforations 120 in the material that further allow the raising of the pull-tab 115. Continued pulling of the pull-tab 115 may then flex the flanges 130 contained within the bumper slot 195 thereby promoting the disengagement of the cover from the vessel and bumper assembly.

Figure 2A:
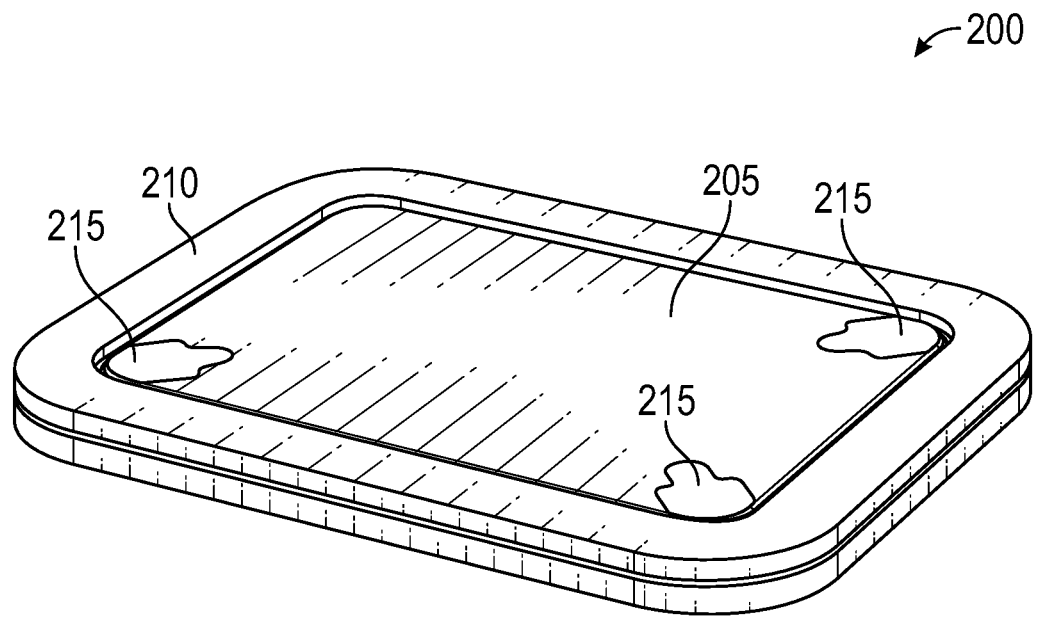
FIG. 2A shows a perspective view of an assembled representation of the vessel assembly shown in FIG. 1.
Figure 2B:
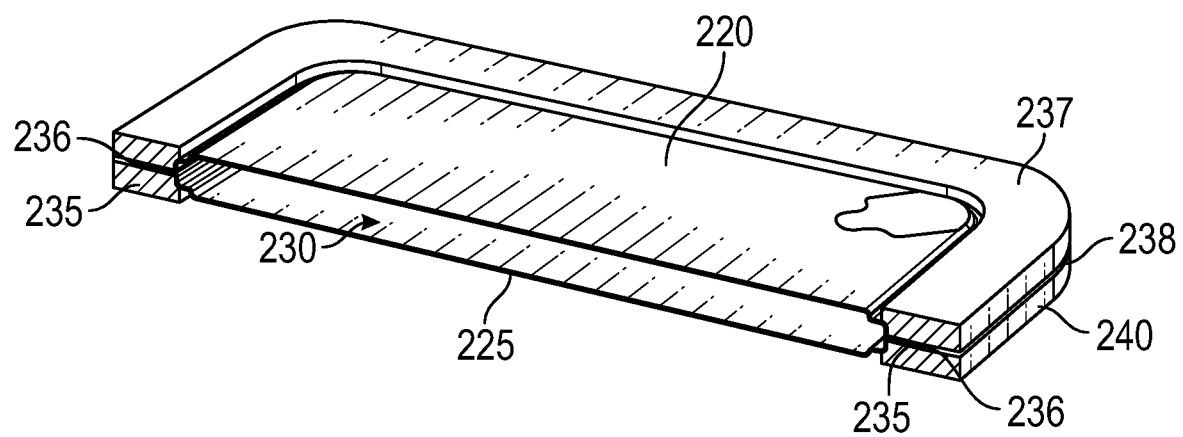
FIG. 2B shows a cross-section view of the assembled embodiment displayed in FIG. 2A
Figure 2C:
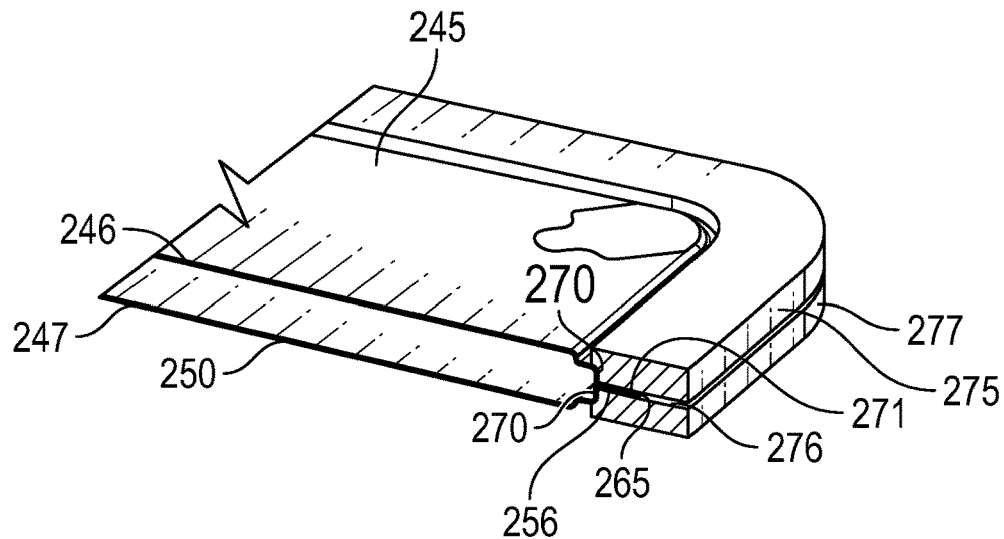
FIG. 2C shows a detailed cross-section view of the assembled embodiment displayed in FIG. 2A.

Now referring to FIGS. 2A, 2B and 2C, various views of an assembled vessel assembly are shown to provide greater detail of the invention previously described and shown in FIG. 1. FIG. 2A, shows a vessel assembly 200 that comprises the containment vessel 205, bumper 210, and sterile port bay covers 215 of the invention as it would appear fully assembled prior to application of the filling procedure described in subsequent figures. Greater detail of the features of the vessel assembly may be observed in FIG. 2B, wherein a cross-section side view is shown. In the embodiment shown, the top shell part 220 has been heat welded to the bottom shell part 225 along the rim flange 235 thereby forming a containment volume 230 into which liquid contents may be introduced. In some embodiments, the shell material comprises one single material that forms the vessel container that completely surrounds the interior containment volume of the vessel 230 and comprises heat weld seams exclusively. In other embodiments, the vessel may comprise more than one material where seams between the different materials are not heat welded prior to the filling and sealing step, however, following the filling and sealing step, these embodiments comprise one single material that is in contact with the vessel interior and completely surrounds the interior containment volume of the vessel 230 and comprises heat weld seams exclusively. In some embodiments, the vessel welded rim flanges 235 are captured within a slot recess in the protective bumper 236. In some embodiments, the protective bumper comprises two or more layers of shock absorbing material. In the embodiment shown, a middle layer 238 of bumper 236 is sandwiched between two outer layers 237 and 240 of bumper 236, wherein the three layers are bonded together. In some embodiments, the layers are bonded by an appropriate bonding method is, for example and without limitation, a stitch bond, thermal fusion bond, or adhesive bond. In some embodiments, the bumper comprises a felt material. In some embodiments, the felt material is a polypropylene felt.

FIG. 2C shows greater detail of the bumper slot and the interaction between the vessel and the bumper, wherein the top shell part 245 and the bottom shell part 250 are joined at the flange rim 256 in a heat weld joint, and wherein the flange rim 256 meets at the outer edge with the middle bumper lamination layer 276 that is sandwiched between the upper bumper layer 275 and the bottom bumper layer 277, and as such, any impact with a lateral vector on the outer surface of the bumper will be absorbed by the bumper material with the load becoming evenly distributed along the outer edge of the vessel flange rim 265. In addition, in some embodiments the bumper frame on the top lamination 275 and the bottom lamination 277 engage with the swept rim 270 of the top 245 and bottom 250 shell parts, thereby increasing the area along which a compressive load may be distributed and thereby increasing the protective properties of the bumper. In some embodiments, a volume 271 between the bumper and the vessel flange and swept rim may be occupied by a portion of a protective cover part (not shown; see FIG. 1, 105, 130), when the protective cover is engaged with the vessel and bumper assembly. In some embodiments, the bumper is a continuous frame into which a shell vessel may be inserted by means of distortion of one of the laminations. In other embodiments the felt bumper frame is interrupted in a lap or scarf joint (not shown) that will facilitate installation and removal of the vessel from the bumper.

In some embodiments, the swept vessel rim on one or both of the shell top 245, or shell bottom 250 parts comprises curvature such that the distance between the planar surface of the upper shell 246 and the bottom shell 247 may be increased or decreased while allowing the surfaces to remain planar through a change in the curvature of the rim profile 270. It may be appreciated by one familiar with the art that aqueous solutions undergoing a solidification phase change expand thereby imposing substantial pressure on any vessel containing the liquid. A vessel wall that is non-pliant will likely fracture under expansion pressure, where a vessel wall that comprises a pliant material will bulge and yield to the expansive pressure. In the embodiment shown in FIG. 2C, distinct performance advantages may be realized if the shell planar surfaces 246 and 247 remain planar following phase change of the vessel contents, therefore applying external forms to the vessel surface that allow an increase in the separation distance between the two surfaces while at the same time imposing a final planar configuration to the surfaces would provide for the realization of these advantages. In some embodiments, a swept rim profile curvature will allow for a change in the distance between the upper shell surface 246 and the lower shell surface 247. Some embodiments comprise a material that will retain a degree of plasticity over the aqueous solution phase change temperature range that is sufficient to allow the necessary change in curvature. In some embodiments, the material is a copolyester polymer. In some embodiments, the copolyester is a Tritan™ copolyester, In some embodiments the Tritan™ copolyester is MP100 provided by the Eastman Chemical Co.

Figure 3:
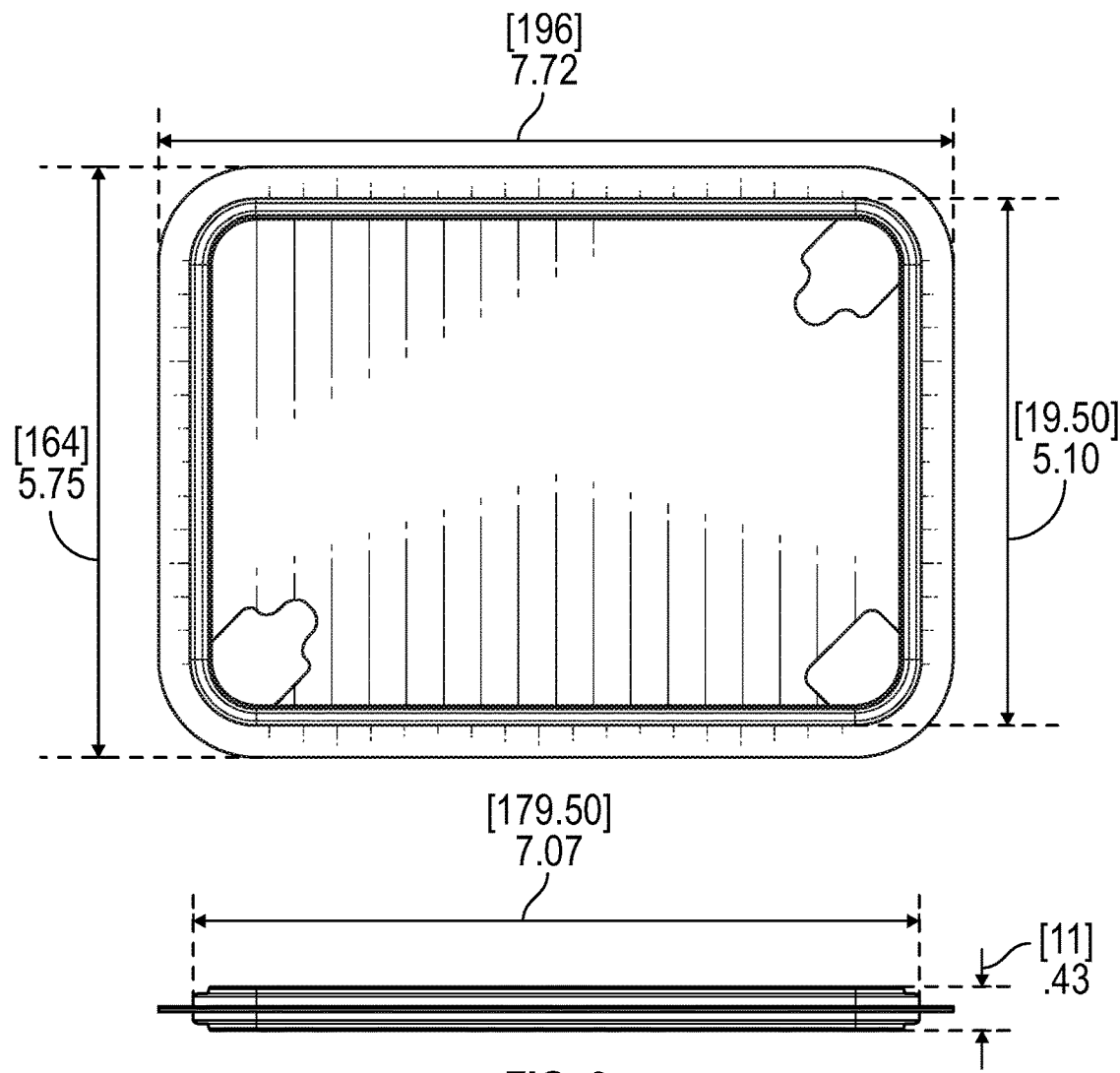
FIG. 3 is a dimensioned drawing of the embodiment of the invention described in FIGS. 1 and 2A-C.

Now referring to FIG. 3, a dimensioned drawing of the embodiment described in FIGS. 1 and 2 is shown. In some embodiments, a vessel contains an internal volume of approximately 220 ml. It may be appreciated by those familiar in the art that all dimensions of the vessel design are independently scalable and therefore vessels with a large range of volumetric capacity may be constructed. It may also be recognized that holding the thickness dimension to the approximate value or less than that shown in the figure will provide the benefits of a large surface area to volume ratio, and that a large surface to volume ratio allows the property of rapid removal or introduction of thermal energy to the vessel. In some embodiments, the volumetric capacity of the vessels will range from 1 ml to 1000 ml. In other embodiments the volumetric capacity will be greater than 1000 ml and less than 1 ml.

Figure 4A:
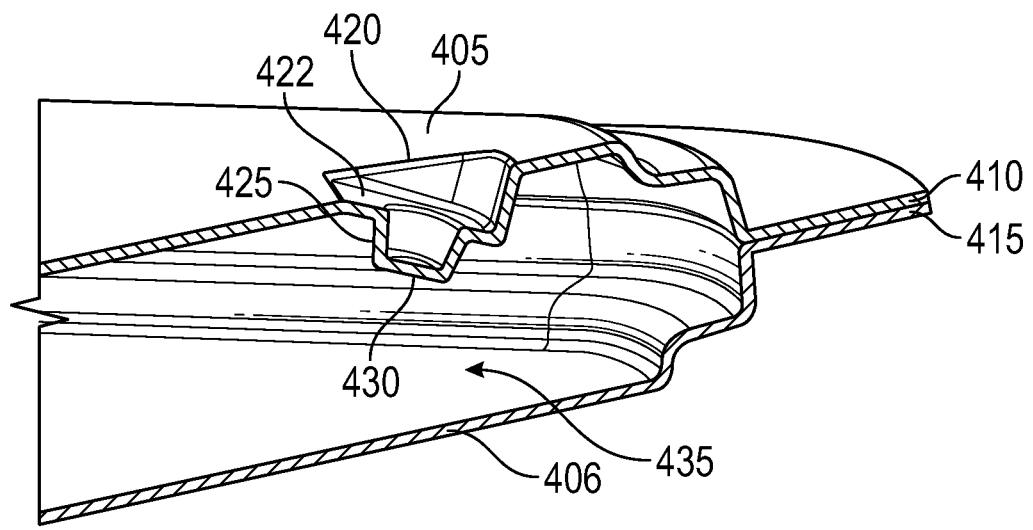
FIG. 4A shows a detailed perspective cross-section view of a port recess in accordance with a representative embodiment of the present invention.

Now referring to FIG. 4A, a detailed cross-section through a corner of a shell vessel is shown, wherein an embodiment of a recessed port bay is installed. In some embodiments, the upper shell part 405 mates with the lower shell part 406 and is joined in a heat weld 410 bond at the flange 415 interface. Into the top surface of the upper shell part 405, a recessed bay port feature 420 is introduced during the molding process. The recessed port bay 420 comprises a flat surface 422 that is positioned at an acute angle relative to the vessel surface 405 on which the port is installed. In some embodiments, the angle of the flat surface 422 relative to the vessel surface 405 may be other than the angle shown in the drawing. In some embodiments, the azimuth of the vector normal to flat surface 422 relative to an axis that is perpendicular to the top surface of the vessel 405 may take on any angular value. In some embodiments, a depression feature 425 is molded in the central area of the flat surface 422 and terminates in a lower surface penetration target 430. In some embodiments, the depression feature is a tapered conical section, as shown. In other embodiments, the depression feature may comprise alternative geometry. In some embodiments, the depression feature comprises a spherical section. In some embodiments, the depth dimension of the depression may be shorter or longer than that shown in the drawing. In some embodiments, the depression feature may comprise a radius value that is shorter or longer than that shown in the figure. In some embodiments, the depression feature is absent.

Figure 4B:
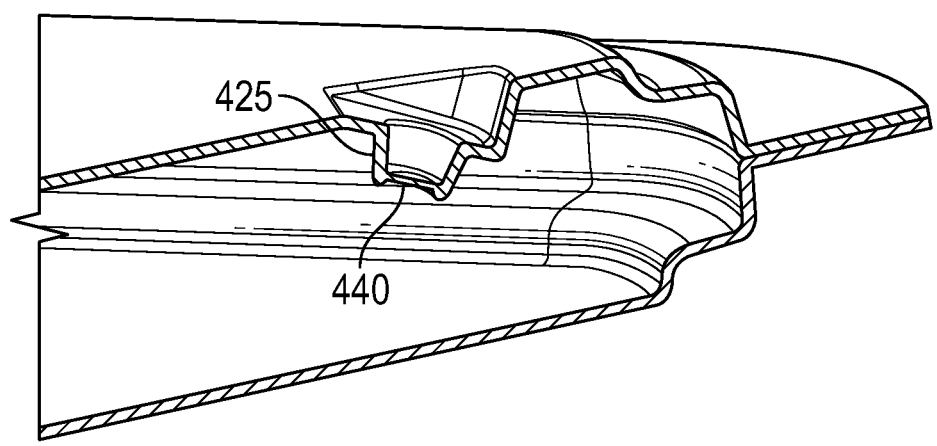
FIG. 4B shows a detailed perspective cross-section view of a port recess in accordance with a representative embodiment of the present invention.

Now referring to FIG. 4B, an embodiment of the recessed port bay described in FIG. 4A is shown wherein the penetration target 440 of the depression feature 425 has been reduced in relative thickness. It may be recognized by one familiar with the art that a thermoplastic material such as a copolyester material will have a greater toughness and resistance to puncture when compared to a rubber material such as a material from which a commercially familiar needle septum stopper would be constructed. Therefore, in some embodiments, it may be necessary to adjust the thickness of the intended target area for penetration of the shell wall by an access instrument such as a hypodermic needle, a symmetric point needle, or a bag port spike in order to modify the force necessary for penetration. As such, in some embodiments, following the molding of the vessel shell part, the depression target 440 may be altered in thickness by local heating and forming, and by this method, the thickness may be precisely adjusted to the appropriate dimension. In some embodiments, the adjusted area is uniform in thickness while in other embodiments, the adjusted area thickness will vary across the area 440.

Figure 4C:
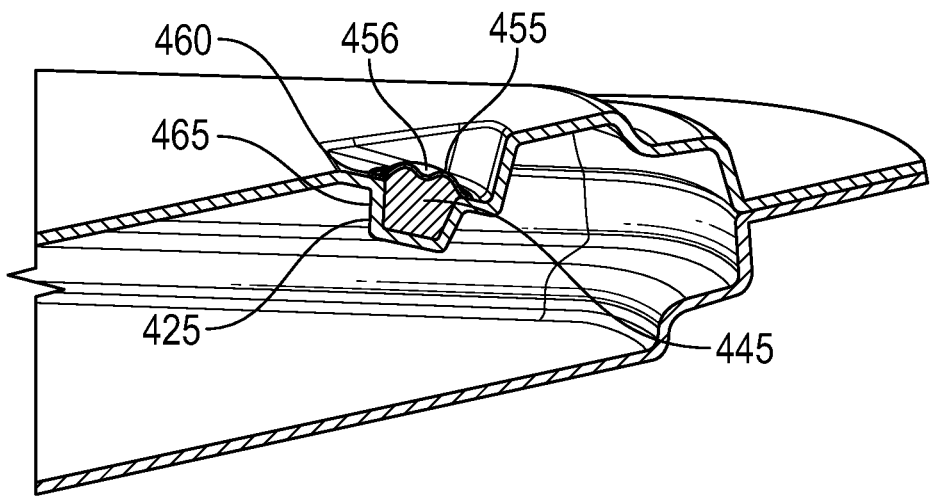
FIG. 4C shows a detailed perspective cross-section view of a port recess in accordance with a representative embodiment of the present invention.

Now referring to FIG. 4C, another embodiment of the recessed port bay described in FIG. 4A is shown wherein the depression feature 425 is shown filled with a material 445 other than that used for the vessel shell. In some embodiments, the material is a rubber material. In some embodiments, the fill material is secured in the depression feature by a thin cap of material 455. In some embodiments, the thin cap material is identical to that used for the vessel shell. In some embodiments, the thin cap is heat welded around the perimeter 460 to the angled face 465 of the recessed bay port. In some embodiments, the thin cap material and fill material comprise a dimple target 456 to facilitate the correct placement of the end of a penetration tool.

Figure 4D:
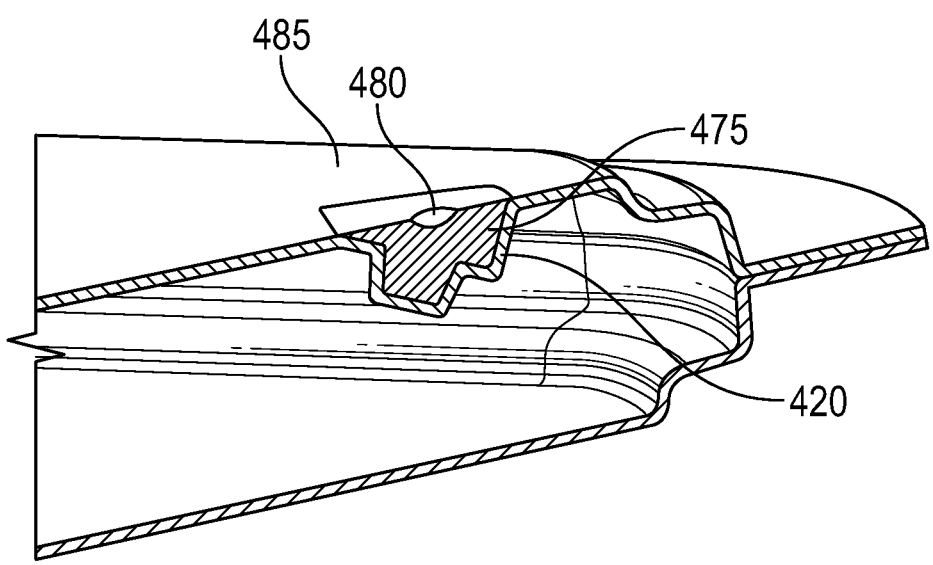
FIG. 4D shows a detailed perspective cross-section view of a port recess in accordance with a representative embodiment of the present invention.

Now referring to FIG. 4D, another embodiment of the recessed port bay described in FIG. 4A is shown wherein the recessed port bay 420 has been filled with a material 475. In some embodiments, the fill material is a rubber material. In some embodiments, a target dimple 480 is molded into the top surface of the material fill. In some embodiments, the rubber material is flush with the surface of the vessel while in other embodiments the material only partially fills the recessed port bay.

Figure 5A:
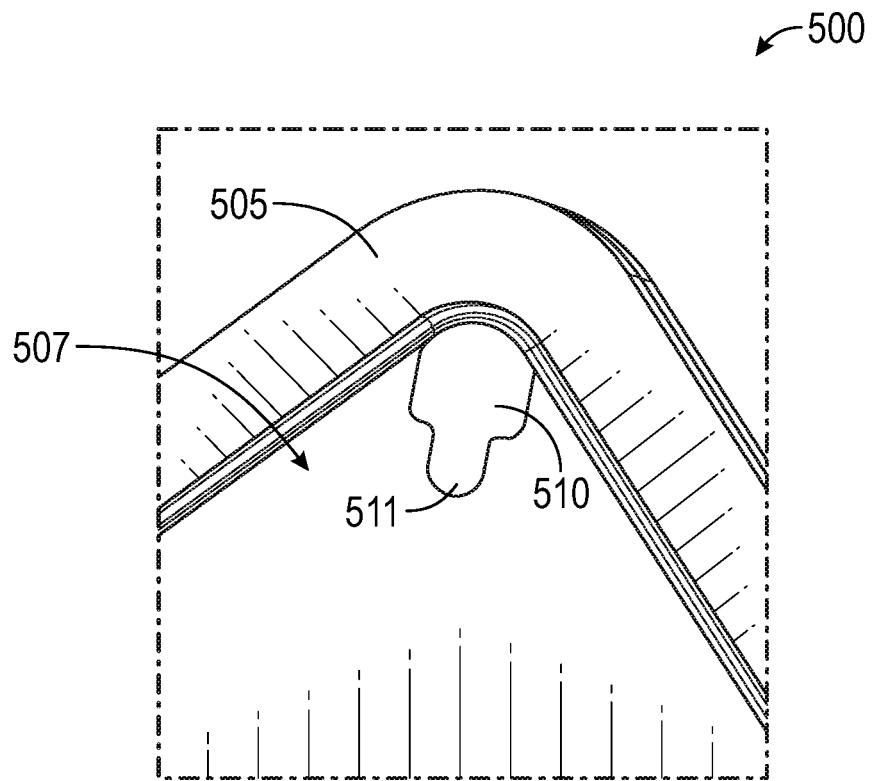
FIGS. 5A-5E show detailed perspective views of a shell storage vessel demonstrating a method by which a shell storage vessel of the present invention is filled and sealed, in accordance with a representative embodiment of the present invention.

Now referring to FIGS. 5A to 5E, one example of one method for filling, sealing, and preparing the vessel container described in the previous figures is shown and described. In FIG. 5A, the representative vessel fill port corner 500 of the vessel is shown in an orientation such that the fill port corner is at a higher elevation that the remainder of the vessel. In the example described, the vessel container shell 507 is surrounded on the flange perimeter by the protective bumper 505, however with some vessel filling protocols, bumper 505 may be absent, and optionally installed in an operation post filling of the vessel. In some filling protocols, the filling operation may be conducted in a cleanroom or sterile area isolated by barriers that will maintain the sterility of the local filling environment. Covering the fill port is a label seal 510 that is reversibly bonded by an adhesive bond to the container shell 507 surface and thereby isolates the fill port recess to maintain sterility of the port recess. The label seal 510 may be removed by placing upward tension on the removal tab 511, thereby initiating a separation of the label from the container shell 507 surface. In some embodiments, the removal tab 511 is not bonded to the container surface 507 thereby facilitating the lifting of the tab. In some embodiments, the tab 511 may comprise extensions or through-holes to facilitate gripping by mechanical filling machinery.

Figure 5B:
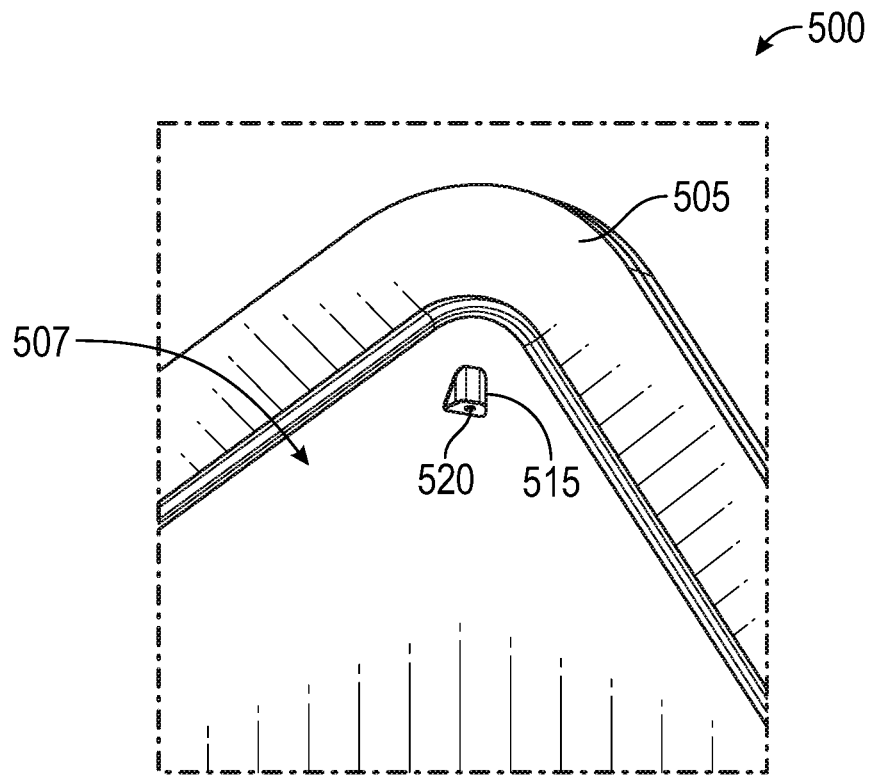

Once the label seal 510 has been removed, now referring to FIG. 5B, the fill port recess 515 is exposed revealing the access target 520. In some embodiments, the access target is a simple dimple in a wall of the recess. In some embodiments, the access target takes on a more complex profile such as a truncated conical indentation, while in other embodiments, the access target comprises more complex features such as, but not limited to, twist lock engagement structures or threaded coupling. In some embodiments, the access target comprises additional materials other than the material from which the vessel wall 507 is constructed.

Figure 5C:
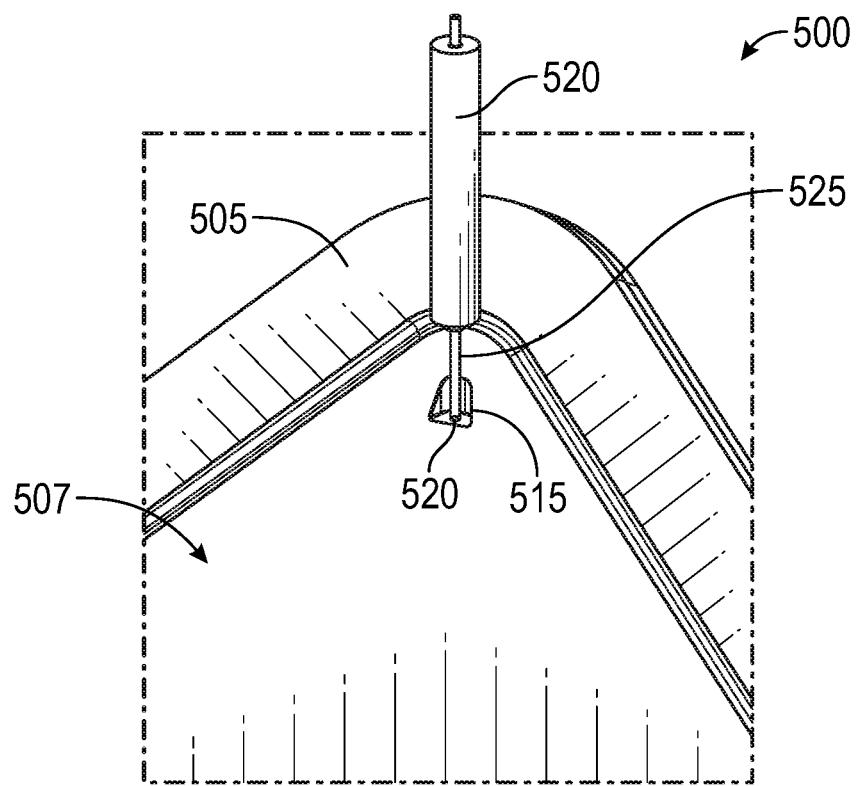

Now referring to FIG. 5C, the access target is penetrated by a filling needle 525 that in some methods may be driven by means of mechanical filling machine elements 520. In some methods, the filling needle 525 has dual countercurrent passageways, one passageway through which liquid may be introduced into the vessel, and another passageway through which gas from the vessel interior may be withdrawn thereby maintaining a pressure equilibrium between the interior of the vessel and the atmospheric environment in which the vessel is resting. When the vessel has been filled to the desired containment volume, in some methods, the filling needle 525 is withdrawn.

Figure 5D:
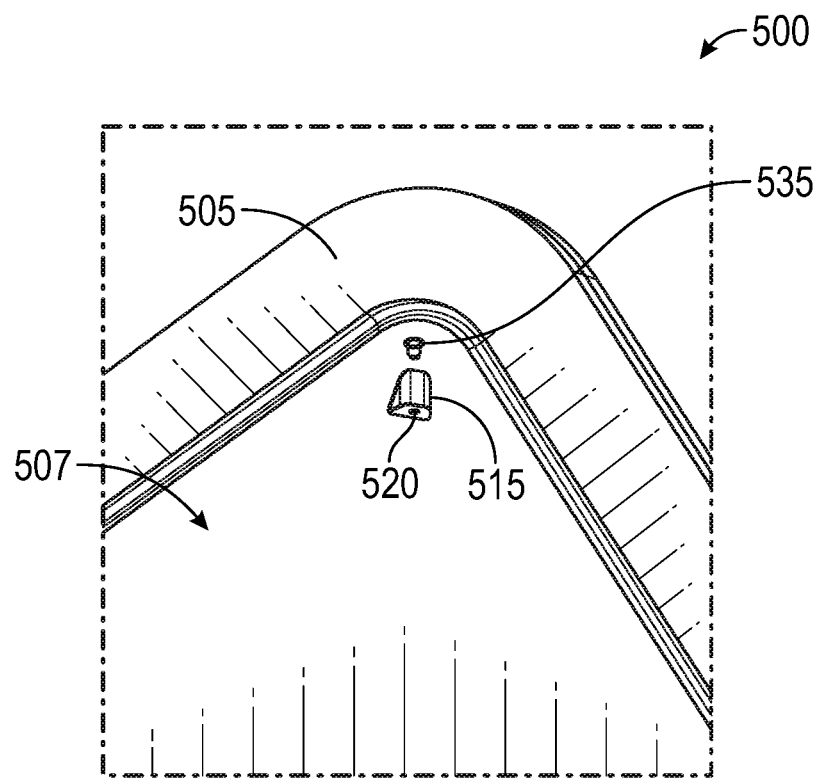

Now referring to FIG. 5D, post filling, in some methods, the access target is sealed by applying a seal element 535 to the access target 520 of the fill port recess 515. In some embodiments, the seal element is plug shape. In other embodiments, the seal element is a cover while in other embodiments, the seal element is a combination of a cover and plug shape. In other embodiments, the seal element may comprise a cup shape such that the seal element may function in a subsequent use method such as venting or vessel contents extraction. In some embodiments, the sealing element material is identical to that from which the vessel has been constructed. In some methods, the seal element, following application to or insertion into the access target 520, is heat impulse sealed (sealing mechanism not shown) to the surface of the fill-port recess 520 such that a fusion of the materials occurs, thereby completely sealing the vessel interior from the external environment.

Figure 5E:
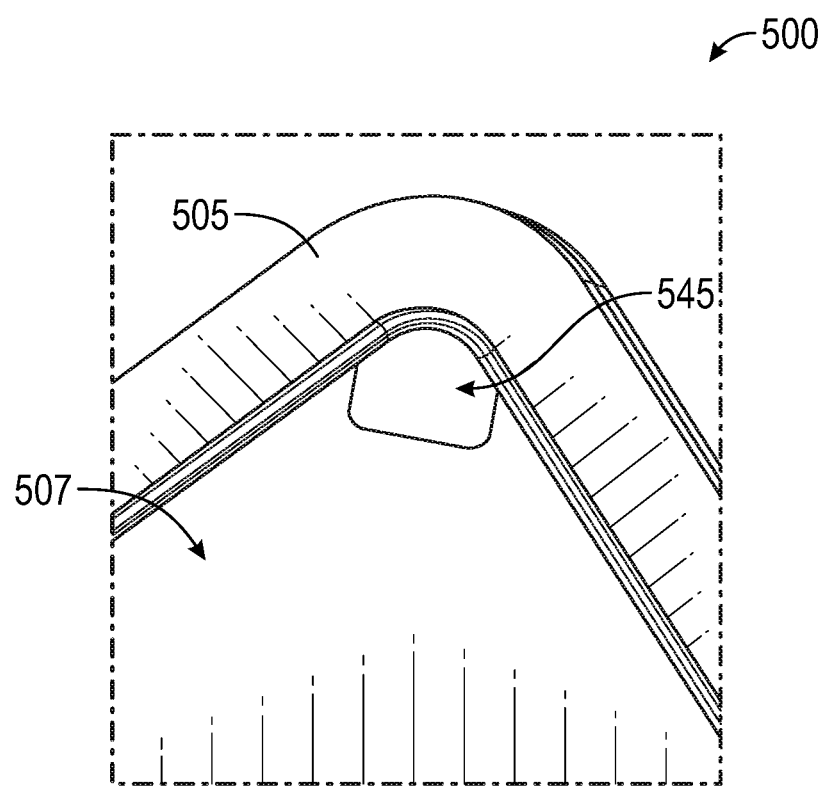

Now referring to FIG. 5E, the final step, in some filling methods, is to apply a sterile seal cover 545 to the vessel shell surface 507 such that the fill port recess (515 in previous figures; here occluded) is isolated from the outside environment. In some embodiments, the seal cover 545 does not comprise a lifting tab (515 in previous figures), as shown in this figure, to designate to the user that this port will not participate in subsequent use operations such as venting or withdrawal of vessel contents. In other embodiments, the tab feature (515 in previous figures) may be present and thereby facilitate the seal 545 removal for subsequent use operations.

Figure 6A:
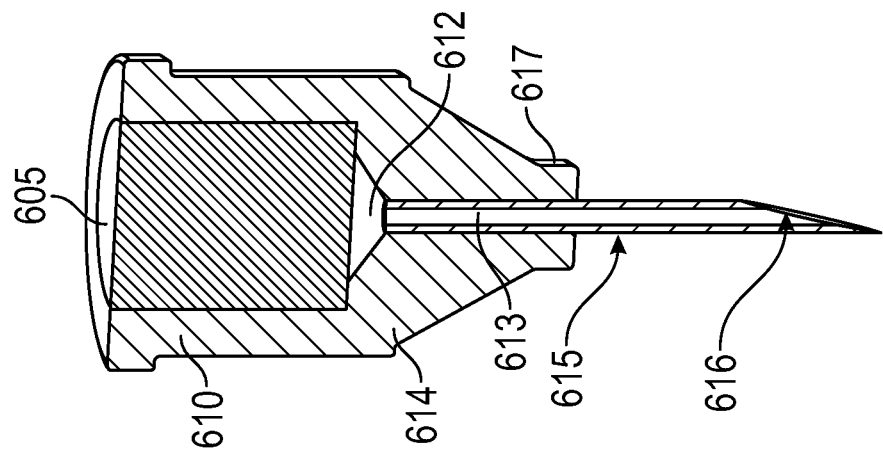
FIG. 6A shows a perspective view and cross-section views of a representative vessel-penetrating sterile filter vent tool that may be used in conjunction with a shell storage vessel of the present invention.
Figure 6A:
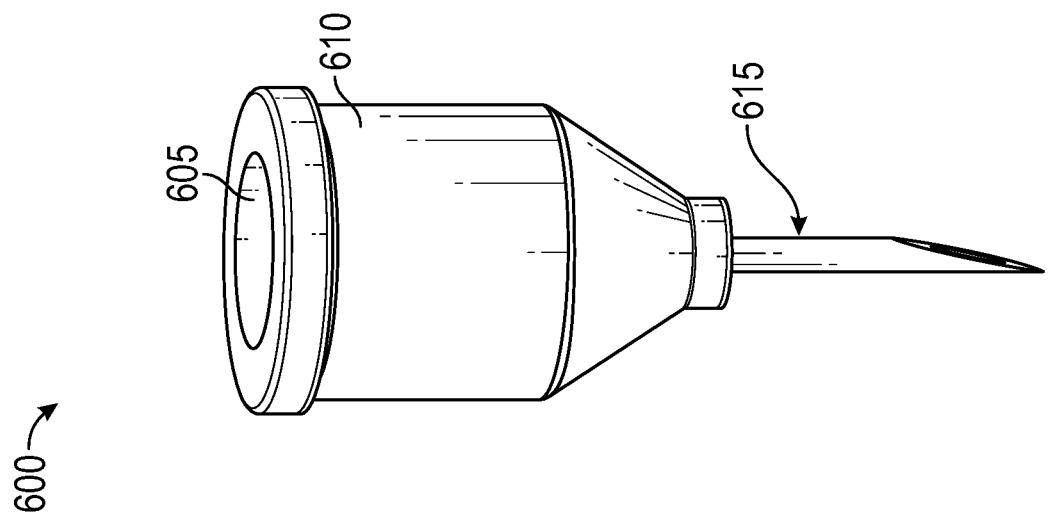

Now referring to FIG. 6A, an example of a sterile venting tool is shown in perspective view and in cross-section of the perspective view. In some embodiments, of the invention, gas will be vented from the external environment to the vessel interior to replace the volume of liquid displaced at the time of extraction of the liquid contents. In some embodiments, during the liquid extraction process, sterility of the vessel interior will be maintained by passing the external gas through a filter with a maximum pore size sufficient to retain pathogenic organisms and prevent entry of the same into the vessel interior. In the example shown 600, a cylindrical container housing body 610 that comprises a cylindrical interior volume that is open at the top end such that the interior volume is continuous with the external environment. Contained within and occupying the entire space of the interior cylindrical volume is a filter element 605 that has a pore size maximum such that any pathogenic biological material in addition to any particulate matter will become entrapped in the filter material while allowing gas to pass through the filtration medium. Filtered gas having passed through the filter 605 will enter the plenum area below 612 and be conducted into the hollow 613 of tubing 615 contained within the cylindrical housing base 614, and exiting at the tubing terminus 616, here shown as a sharpened bevel in the tubing 615. In some embodiments, the filter (as a prepared accessory) may be attached to a needle cover that reversibly binds by friction to the cylindrical extension 617 of the filter housing, and thereby maintains the sterility of the needle until use.

Figure 6B:
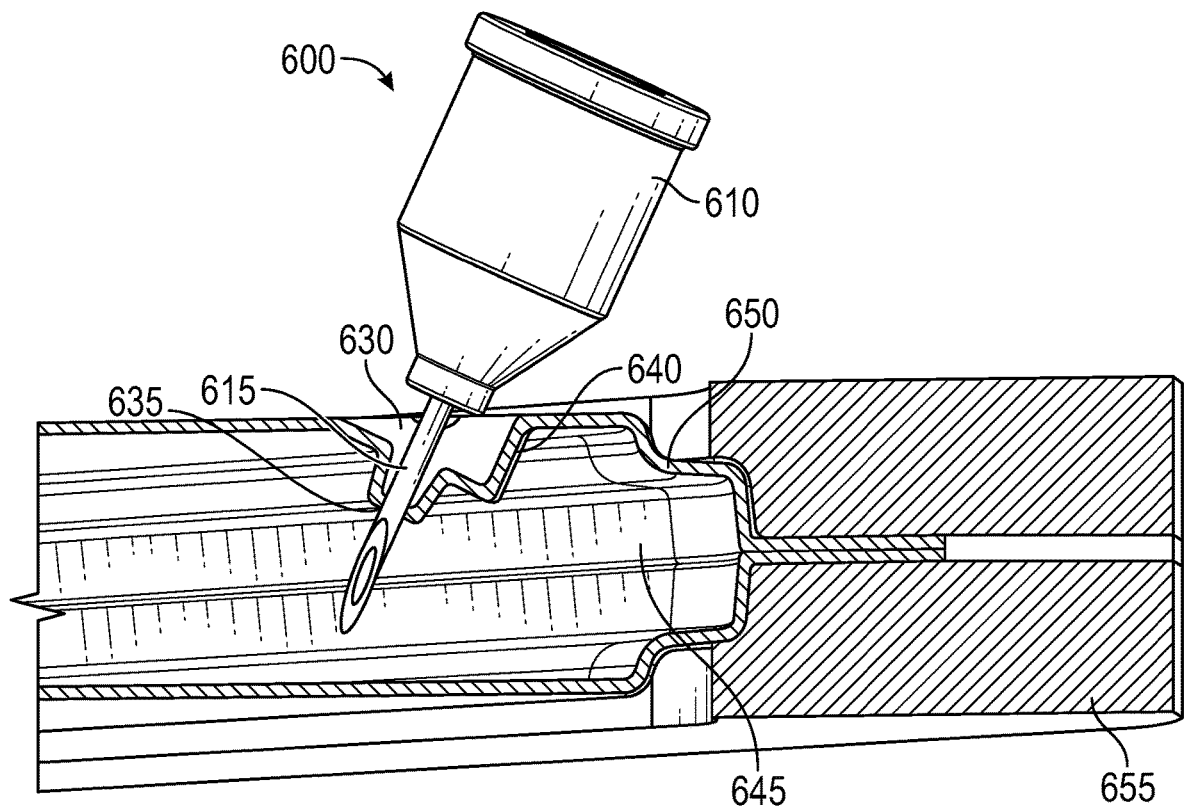
FIG. 6B shows a partially cross-section side view of a shell storage vessel penetrated by a sterile venting tool, wherein this figure demonstrates a method by which the shell storage vessel is vented, in accordance with a representative embodiment of the present invention.

Now referring to FIG. 6B the method for the venting of a vessel embodiment of the invention is shown. In the illustration, a cross-section of the vent port corner of the vessel shell 650 and bumper felt bumper frame 655 is provided. A sterile venting tool 610 (as described in FIG. 6A) is shown inserted through the rubber filling 630 that fills the vent port 640 that is continuous with the upper shell of the vessel 650 and also through the access target 635 of the recessed port 640, thereby penetrating the continuous shell boundary that previously completely enclosed the vessel interior 645, and thereby creating a pathway through which gas from the external environment may pass into the vessel interior 645 by way of flow through the sterile filter (element 605 in FIG. 6A). In some embodiments, the access target 635 material at the boundary of the filtration vent needle 615 forms an airtight seal sufficient to prevent gas flow between the access target material 635 and the filtration vent needle 615. In other embodiments, an airtight seal is made between the fill material 630 and the needle 615, while in other embodiments, a seal with the needle is made by other structures, such as and without limitation, the fill material 445 and cap structure 455 described in FIG. 4C.

Figure 7:
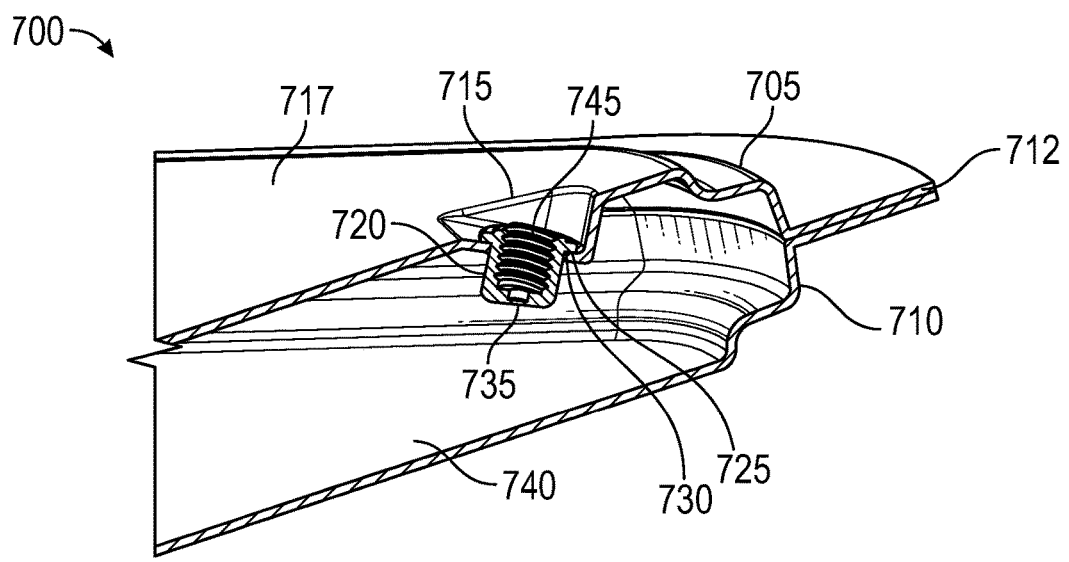
FIG. 7 shows a detailed perspective cross-section view of a port recess comprising a injection-molded element welded therein and having a threaded interface for attachment of external accessories, in accordance with a representative embodiment of the present invention.

Now referring to FIG. 7, a cross-section view of an embodiment of the invention is shown wherein a first shell part 705 is mated to a second shell part 710 at the flange boundary 712 of both parts, where a port recess 715 is present in the major surface 717 of the first shell part 705, and where a through-hole has been introduced into one surface 730 of the port recess 715, into which a threaded insert part 720 has been inserted such that the undersurface of a flange 725 of the insert 720 is in contact with and mated to the surface 730 of the port recess 715. In some embodiments, the threaded insert 720 is heat welded to the port recess surface 730 such that the interior of the vessel 740 is isolated from the exterior environment of the vessel. In some embodiments, the insert 720 is constructed from the same material that is used to form the first shell part 705 and the second shell part 710. In some embodiments, the insert 720 is made by an injection molding process. In some embodiments, the insert 720 comprises an internal thread 745 by which external coupling devices may securely interact with the recess port insert. In some embodiments, one underside wall of the insert 720 may comprise a second thickness 735 to adjust the necessary force required to penetrate the wall by an instrument when coupled to the insert 720.

Figure 8A:
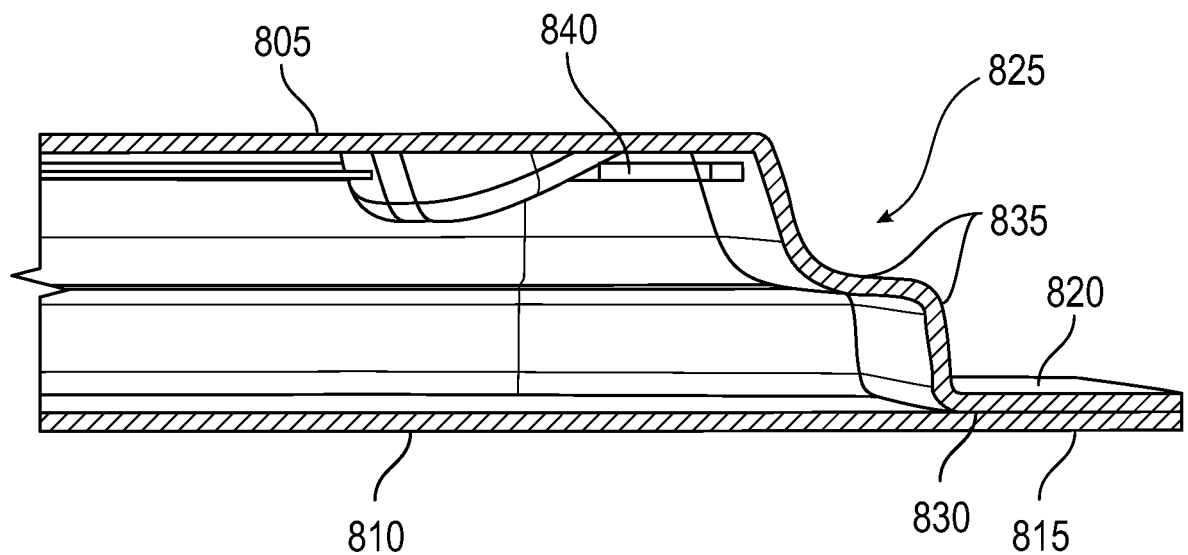
FIG. 8A shows a detailed cross-section view of a shell storage vessel having a swept-rim profile and a planar wall enclosing the vessel, in accordance with a representative embodiment of the present invention.

Now referring to FIG. 8A, an embodiment of the invention is shown in cross-section. In this embodiment, an upper shell part 805 is joined with the second or lower vessel planar shell part 810 in a fusion bond of the material around the perimeter flange 820 of the upper shell part 805 and the opposed material of the second or lower shell part 815. One familiar with the art will recognize that when filled with an aqueous solution and placed in a temperature environment that is below the freezing point of the solution that an expansion of the contents will occur during the solidification process. To allow for an expansion of the vessel under the outward pressure of the material undergoing phase change upon the interior surfaces of the vessel, in some embodiments, the swept rim 825 may comprise a profile with curvature 835 such that a change in curvature when pressure is applied to the inside surface of the profile will allow the distance between two shell part surfaces 825 and 810 to increase without distortion of the shell part planar surfaces 805 and 810 and without placing excessive stress on the fusion bond 830 between the upper shell rim flange 820 and the opposed part 815 of the second shell part 810. In some embodiments, external forms may be applied to the vessel during the freezing process to limit any change in shape to the vessel shell wall except at the swept rim 825.

Figure 8B:
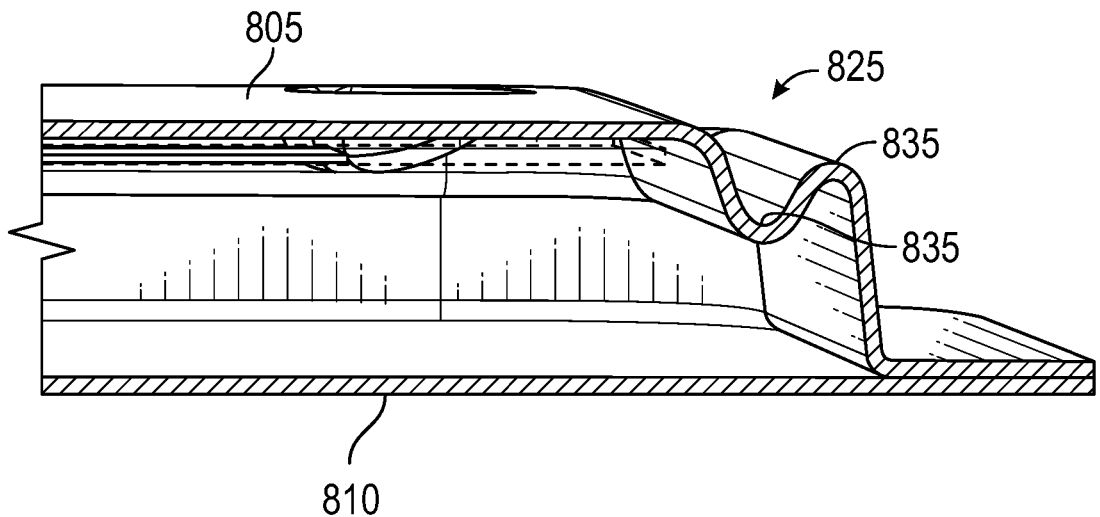
FIG. 8B shows a detailed cross-section view of a shell storage vessel having a swept-rim profile and a planar wall closing the vessel, in accordance with a representative embodiment of the present invention.

Now referring to FIG. 8B, a cross-section of the vessel shown in FIG. 8A is shown wherein the swept rim 825 comprises a more exaggerated double-back curvature 835 than the rim counterpart shown in FIG. 8A. In some embodiments, the length of the profile line that defines the swept rim 825 is increased such that a greater range of extension of the swept rim is possible as distance between the planar surfaces of the upper shell part 805 and the bottom planar shell part 810 is increased.

Figure 9A:
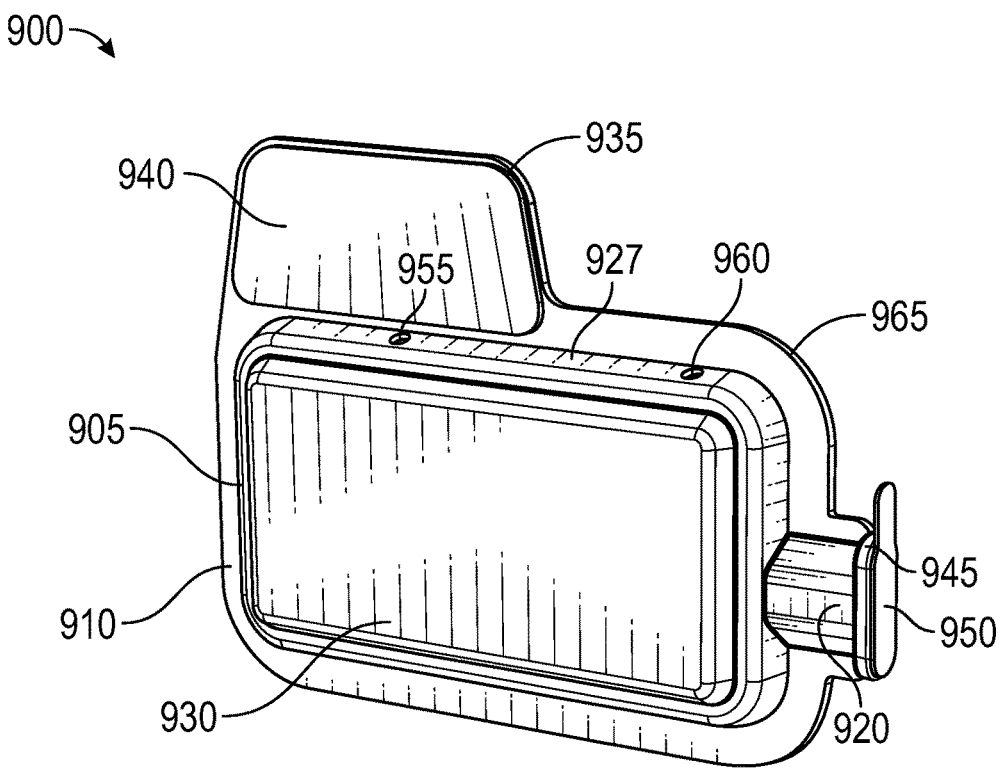
FIG. 9A shows a perspective view of a shell storage vessel having a rim extension that allows the vessel to be filled through a channel that extends through the swept rim, in accordance with a representative embodiment of the present invention.

Now referring to FIG. 9A, an embodiment of the invention is shown comprising a first or upper shell part 905 shell comprising a major planar surface 930 with rounded corners joined with a swept expandable rim 927 that is further joined with a flange rim 910, the first or upper shell part 905 being bonded to a planar second or lower shell part 965 (occluded behind the upper shell part 905). Interrupting the flange rim of the first shell part 905 is an extension 920 of the swept rim 927 forming all sides of a conduit tunnel, with the exception of the side formed by the second part, the conduit tunnel forming a passageway between the vessel interior volume and the exterior environment. In some embodiments, the conduit tunnel terminates in an end plug 945 that is heat welded to the material forming all sides of the conduit tunnel, the end plug 945 further comprising one or more through-holes, apertures, lumens or pathways by which material may be introduced into the vessel interior. In some embodiments, the end plug 945 through-holes are closed by a reversibly bonded airtight seal label 950 configured to isolate the interior of the vessel until removed. In some embodiments, the vent port 955 and the extraction port 960 are located within the wall of the swept expansion rim 927. In some embodiments, the flange 910 is joined with an extension 935 that may serve as a handle for manual or mechanical transfer of the vessel, thereby isolating the remainder of the vessel from the thermal energy influx from the gripping element. In some embodiments, the surface flange extension 935 provides a plane onto which an identifying label 940 may be affixed. In some embodiments, the flange extension 935 and affixed label 940 allows the vessel 900 to be stored in a lateral stacking configuration with the extensions and labels extended upward to facilitate rapid identification and location of a selected vessel from a collection of like vessels. In some embodiments, the flange extension 935 and the affixed label 940 may serve to reduce the time necessary for location of a specific vessel thereby mitigating the rise in temperature and damaging thermal cycling to contained samples associated with holding a collection of vessels at room temperature while such a search is conducted. In some embodiments, the first or upper shell part 905 and the second or lower shell part 965 are partially bonded at the location of the flange extension 935 such that a two-sided container is formed between the two parts. In some embodiments, the flange extension two-sided container may enclose an electronic identification device. In some embodiments, the electronic identification device is an RFID chip.

Figure 9B:
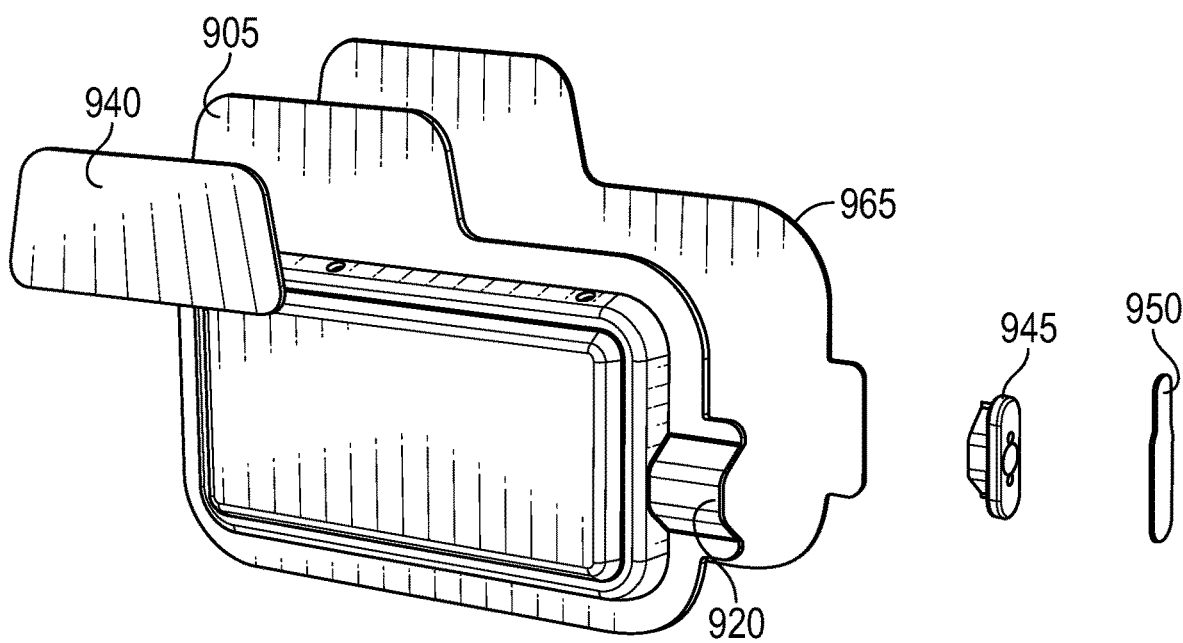
FIG. 9B shows an exploded view of the embodiment shown in FIG. 9A.

Now referring to FIG. 9B, an exploded view of the vessel described in FIG. 9A is shown to better illustrate the construction of the vessel. In some embodiments, the first or upper vessel shell part 905 mates with the second or lower planar vessel shell part 965. In some embodiments, the second vessel shell part 965 is non-planar and comprises a cavity. In some embodiments, the second vessel shell part 965 is a nominal mirror image at the flange plane bonding surface of the first shell part. In some embodiments, an injection-molded insert plug 945 is heat welded to form a complete seal with the first shell part 905 and the second shell part 965 in the through-tunnel, through-hole, aperture, lumen or other pathway formed by the swept rim extension 920 of the first shell part 905 and the opposing area of the second shell part 965. In some embodiments, the plug cap 945 is reversibly sealed by the attachment of an airtight label cover 950. In some embodiments, an identification label 940 may be applied to the exterior surface of the either the first shell part or the second shell part.

Figure 9C:
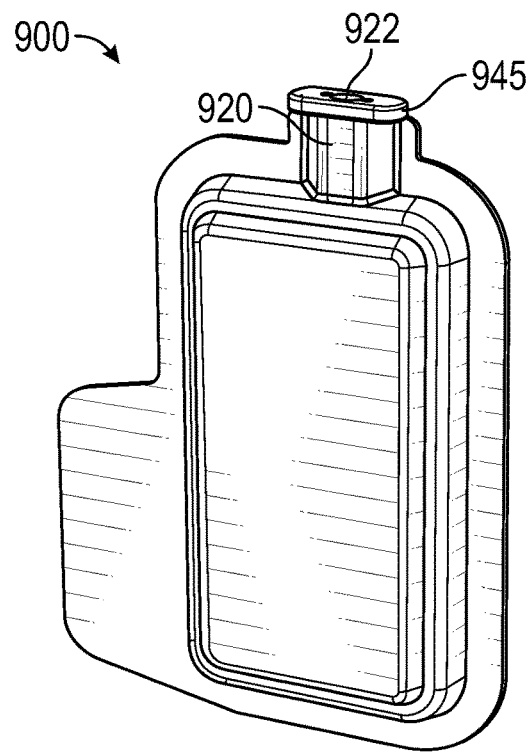
FIG. 9C shows a perspective view of the embodiment shown in FIG. 9A in a first stage of vessel filling, in accordance with a representative embodiment of the present invention.

Now referring to FIG. 9C, the first stage of a method of filling the vessel 900 described in FIGS. 9A and 9B is shown. In some methods, the sterile label seal (FIG. 9A, 950) is removed thereby exposing the through-hole passageway 922 that extends from the top exterior surface of the through-tunnel 920 end cap 945 to the vessel interior, and the vessel 900 is positioned in an upright orientation with the end cap 945 located at the highest elevation. In some embodiments, the liquid contents of the vessel may be introduced into the vessel interior by means of a tubular filling needle. In some methods, an air space remains after the introduction of the vessel contents such that the liquid inside the vessel does not occupy the through-tunnel passageway 920.

Figure 9D:
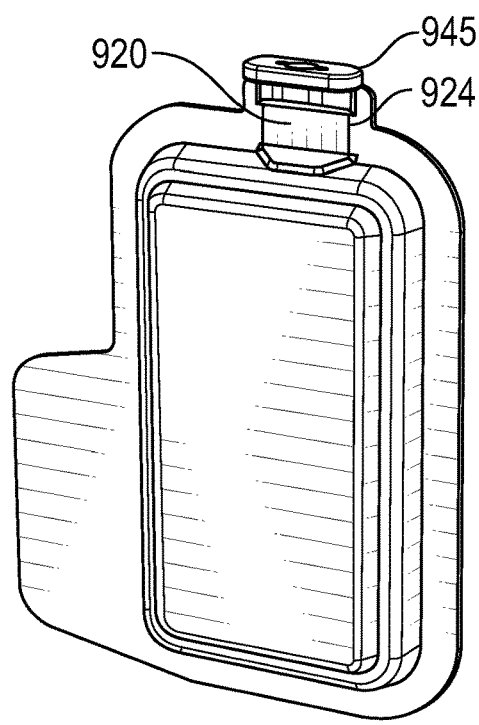
FIG. 9D shows a perspective view of the embodiment shown in FIG. 9A following filling and sealing stages, in accordance with a representative embodiment of the present invention.

Now referring to FIG. 9D, the second stage of a method described in FIG. 9C is shown. In some methods, with the vessel kept in the upright orientation as in FIG. 9C, the filled vessel through-tunnel 920 is collapsed by clamping the passageway 920 in a heater device (not shown) and raising the temperature of the passageway material to the glass and fusion temperature of the material, thereby flattening the passageway to the thickness of the adjoining flange. In some methods, the clamping and heating device comprises a trimming feature whereby the end cap 945 and adjoining vessel material may be removed from the remainder of the vessel at the line indicated 924 such that the trim line is coincident with the outside edge of the rim flange at 924. In some methods the thermal compression and heating device seals the vessel along the pathway of the vessel flange such that the flange seal is continuous around the vessel perimeter thereby isolating the vessel contents from the external environment.

Figure 9E:
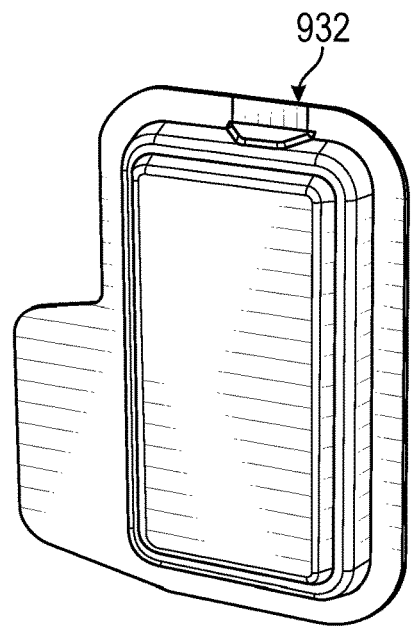
FIG. 9E shows a perspective view of the embodiment shown in FIG. 9A having been sealed and the filling access port being trimmed away, in accordance with a representative embodiment of the present invention.

Now referring to FIG. 9E, the third stage of the method described in FIGS. 9C and 9B is shown. In some methods, upon cooling of the sealed and trimmed vessel along the flange perimeter 932, the vessel sealing is complete, and the vessel and the contents may be furthered processed by subsequent methods, such as freezing, storage, transport, and thawing methods.

Figure 9F:
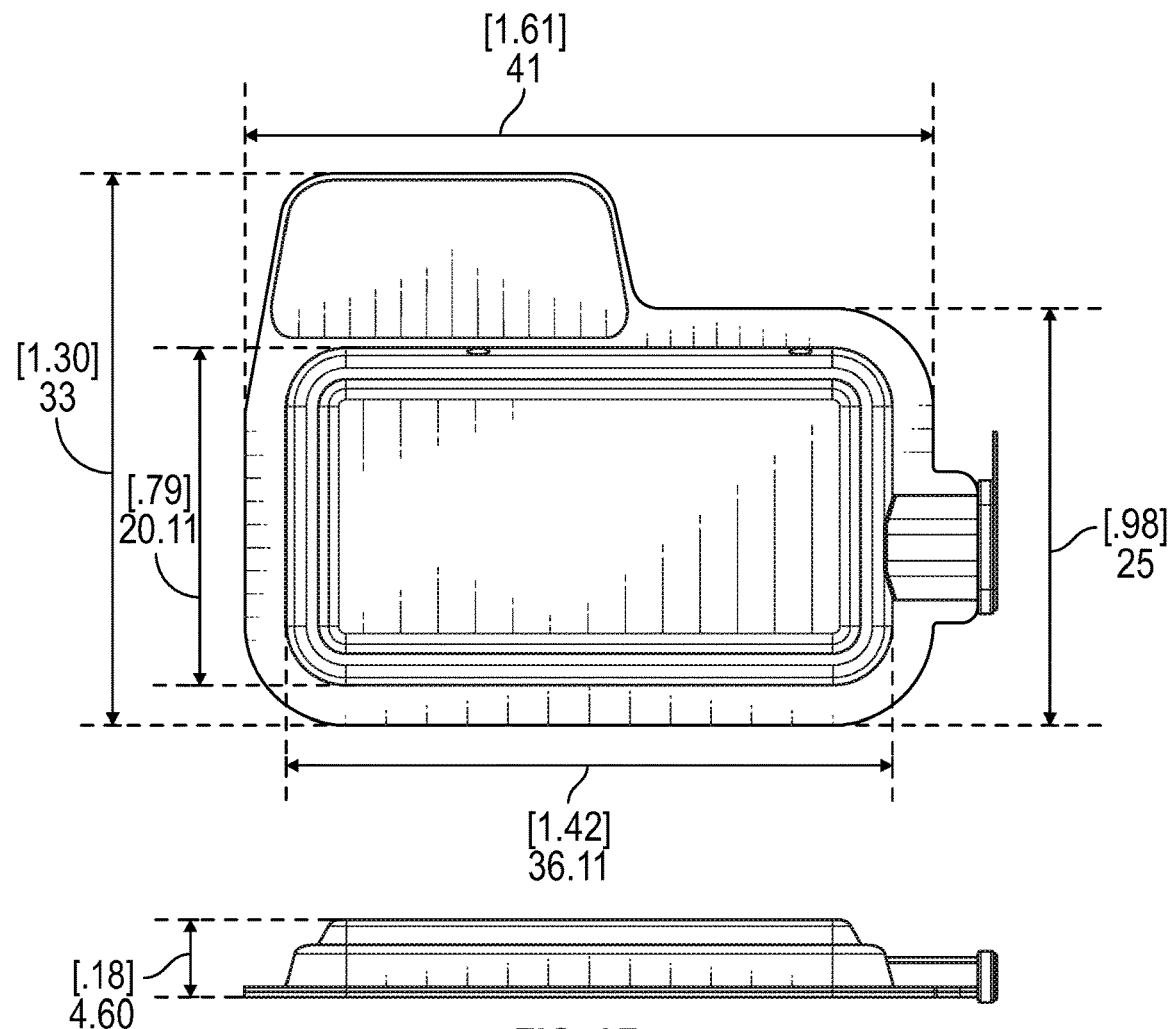
FIG. 9F shows a dimensioned drawing of the embodiment described in FIG. 9A.

Now referring to FIG. 9F, a dimensioned drawing of the embodiment shown in FIGS. 9A through 9E is shown. The vessel embodiment shown has a nominal volumetric capacity of 2 ml. In some storage methods, the dimensions shown may be stored in a common 5 inch by 5 inch cryostorage box in three columns of twenty-seven rows for a total of eighty-one vessels per box. In some methods, the identity of a specific vessel, even without prior knowledge of the position of the vessel, may be assessed visually by scanning the rim extension labels without handling and raising the vessel as would be necessary for a similar array of cylindrical tubular vial with labels affixed on the sides.

Figure 10A:
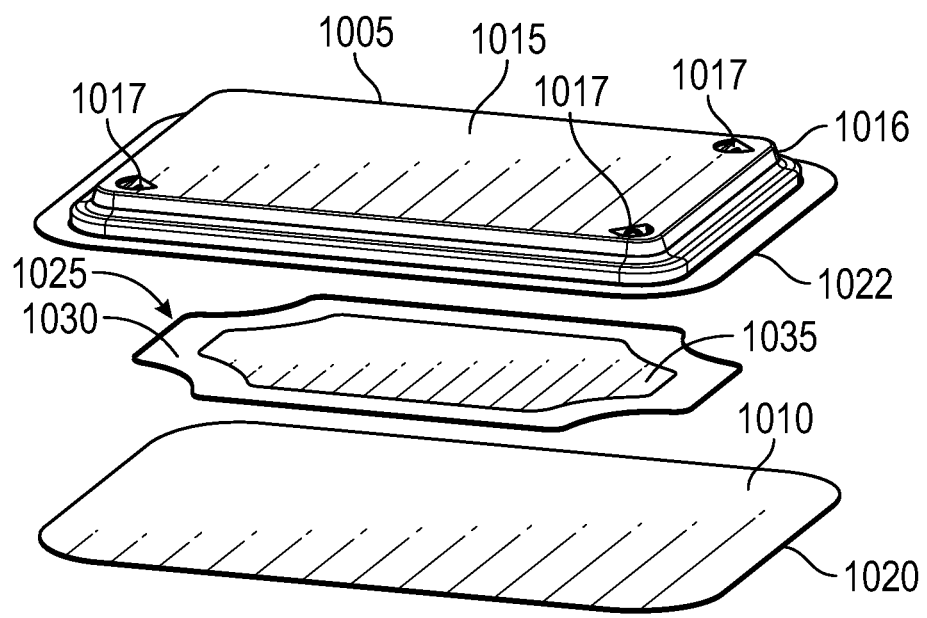
FIG. 10A shows an exploded view depicting the key elements of an embodiment of the invention having a flat plane vessel wall abutting the flange joint and comprises an internal driver card vessel solid content-biasing element, in accordance with a representative embodiment of the present invention.

Now referring to FIG. 10A, an exploded view of another embodiment of the invention is shown wherein a first or upper shell container part 1005 with an internal volume boundary comprised of a flat planar surface 1015 surrounded by a complex profile swept rim 1016 and a peripheral flange 1022 extending from the bottom edge of the rim 1016, and in which one or more recessed port structures 1017 are contained within. In some embodiments, the second or lower shell container part of the vessel is a flat planar part 1010 which mates and is bonded in a heat weld or other suitable joint with the upper shell container part 1005 at the flange rim 1022 where it meets the peripheral margin 1020, thereby creating a vessel shell body with two parallel and opposed flat planar surfaces. In some embodiments, the swept rim 1016 flares outward from the upper surface 1015 with no undercut surfaces, such that any solidified contents with the container upon detachment from the upper shell interior surface is permitted to move in a direction vector perpendicular to the top planar surface of the vessel without any interference by the upper shell part 1015. In some embodiments, a driver card element, component or part 1025 is contained within the vessel interior volume. In some embodiments, the driver card 1025 comprises a ferritic flat part 1035 that is laminated between two layers of material 1030 that are joined on the margin in a heat weld or other suitable bond, such that the ferritic part 1035 is completely surrounded by the laminating material 1030. In some embodiments, the laminating material 1030 is identical to the material used for the vessel shell parts.

Figure 10B:
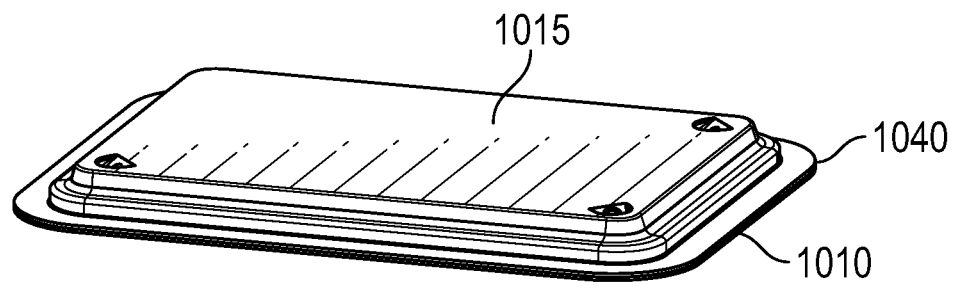
FIG. 10B shows a perspective view of an assembled representative of the embodiment shown in FIG. 10A.

Now referring to FIG. 10B, the upper shell 1015 is shown joined to the underside flat surface 1010 at a heat weld bond 1040 to form the complete vessel structure. In some embodiments, the underside flat surface 1010 allows a planar heater surface to contact the underside surface thereby increasing the temperature of the contents contained within.

Figure 11A:
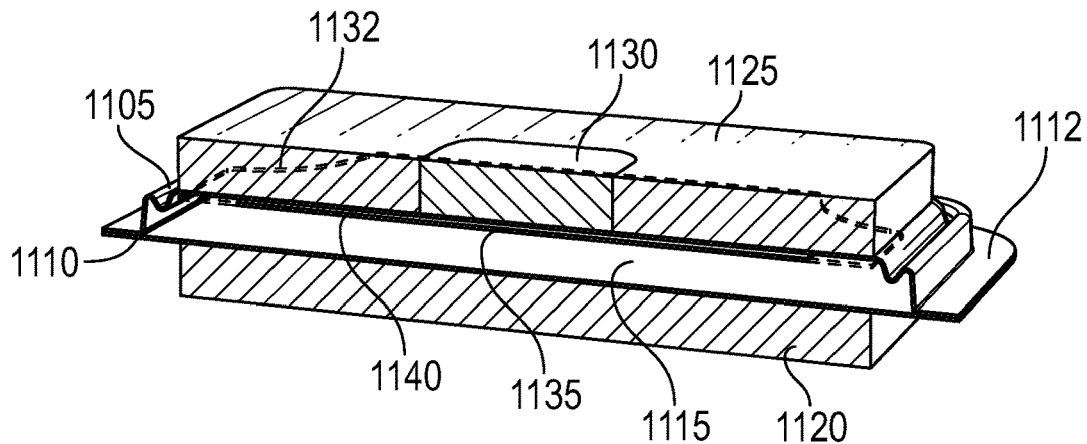
FIG. 11A shows a cross-section view of the embodiment shown in FIG. 10B in contact with a cross-section view of a representative freezing device for the purpose of illustration of an initial stage of a method of use example, in accordance with a representative embodiment of the present invention.

Now referring to FIG. 11A, the first stage of a thawing sequence progression is shown to illustrate a method by which the freezing and thawing of the vessel contents may be conducted. In FIG. 11A, a cross-section view of the vessel described in FIG. 10 is shown wherein the upper shell 1105 of the vessel and the flat planar bottom part of the vessel 1110 are joined around the peripheral flange 1112 in a heat weld joint. The interior volume of the vessel 1115 for the purpose of the explanation of the process method is assumed to be filled with an aqueous liquid. The vessel interior also holds a driver card 1140 comprising a ferritic plate 1135 laminated between two sheets of the same material used for the vessel wall (laminated sheets are shown in transparency), wherein the ferritic plate 1135 of the driver card 1140 is held or selectively suspended in contact with the top inner surface of the upper shell part 1105 through the attraction of a magnet 1130 that is embedded into a block of thermally conductive material 1125. An additional block 1120 that is constructed from a thermally conductive material is in direct contact with the underside of the vessel 1110. In this phase of the method, both blocks 1125 and 1120 are reduced in temperature such that thermal energy is conducted away from the vessel and the vessel contents until a phase change occurs in the liquid contents. Upon solidification, the upper block 1125 and magnet 1130 and the lower block 1120 are removed leaving the driver plate 1140 captured in a static position by the solidified contents.

Figure 11B:
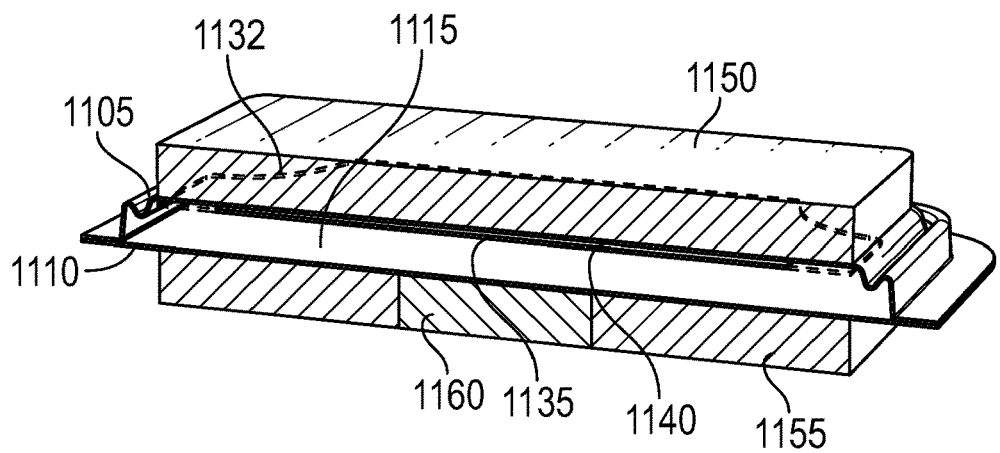
FIG. 11B shows a cross-section view of the embodiment described in FIG. 10A in contact with a cross-section view of a representative freezing device for the purpose of illustration of a later stage of the method of use example illustrated in FIG. 11A.

Now referring to FIG. 11B, the vessel and contents described in FIG. 11A with the vessel contents 1115 in a solidified state is shown. At this step of the method, the upper shell 1105 and the lower planar shell part 1110 forming the complete vessel are now clamped between a heater block 1150 that is in direct contact with the upper flat surface of the vessel 1105 and a second heater block 1155 that is in direct contact with the lower flat surface of the vessel 1110. Embedded in the lower heater block 1155 is a magnet 1160. When the solidified contents of the vessel 1115 increases in temperature to a value that is sufficient to allow separation of the solidified contents from the inner surface of the upper shell, the magnetic attraction of the magnet 1160 on the driver card 1040 will bias the solidified contents to the interior surface of the lower flat vessel part 1110. At this point in the method, the upper heater block may be de-energized so that it is no longer in a heating mode or, alternatively, may be withdrawn from contact with the outer surface of the upper vessel shell part 1105. As a phase change of the solid vessel contents 1115 occurs at the interior surface of the flat vessel shell part 1110, the bias pressure of the driver card 1140 will force the liquid forming at the interior surface of part 1110 to the perimeter and subsequently to accumulate between the driver card 1040 and the inner surface of the upper shell part 1150. As this process progresses, only solidified vessel contents 1115 will be in contact with the inner surface of the flat vessel part 1110, and therefore will act as an efficient heat sink for thermal energy provided by the lower heater block 1155, with temperatures at the solid material 1155 remaining at a temperature close to the phase change temperature of the solid material 1115, therefore a high wattage influx of thermal energy may be applied to the thawing process resulting in reduced phase change intervals without risk of damage to the liquid contents due to elevated temperatures.

Now referring to FIG. 11C, a time later in the thawing process than that depicted in FIG. 11B is shown. At this stage of the thawing process, the upper heater block 1150 has been de-energized, although still shown in contact with the top flat surface of the upper shell part 1105. As the thawing process has progressed at this stage of the process, the solid material contents 1115 of the vessel has decreased and the driver card 1140 is at a lower position within the vessel interior. Likewise, the volume of the liquid contents accumulating in the space 1175 above the driver card 1140 has increased. During this phase of the thawing process, the heater block 1155 may, in some methods, still be producing a high wattage output for thermal energy. In some embodiments, the upper heater block 1010 may be actively chilled to control the temperature of the liquid contents of the space beneath. In some embodiments, the proximity of the driver card may be monitored by a hall sensor, or inductive sensor (not shown) embedded in or near to the heater block 1155 to determine the status of the thawing process and determine the eventual completion of the thawing process.

Figure 11C:
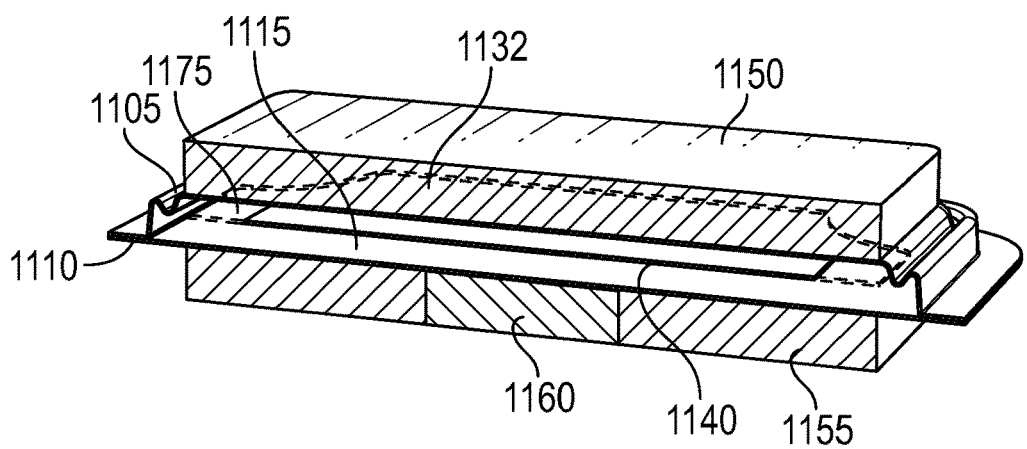
FIG. 11C shows a cross-section view of the embodiment described in FIG. 10A with a cross-section view of a representative freezing device for the purpose of illustration of a later stage of the method of use example illustrated in FIG. 11B.
Figure 11D:
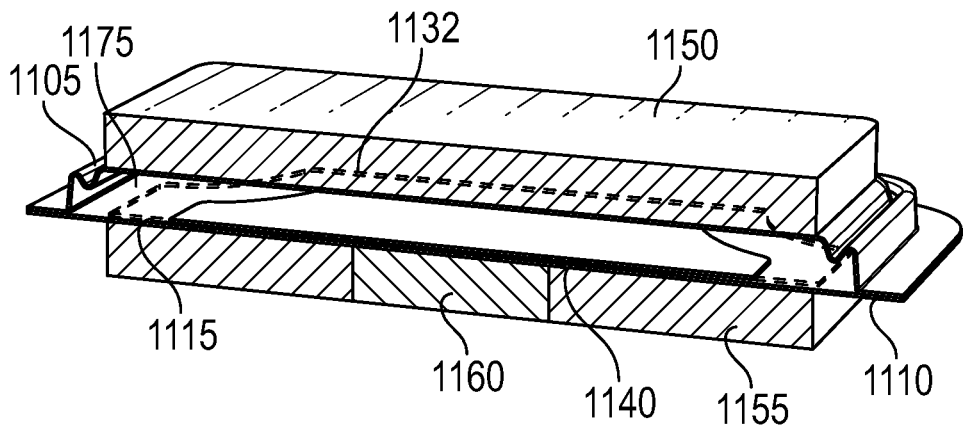
FIG. 11D shows a cross-section view of the embodiment described in FIG. 10A with a cross-section view of a representative freezing device for the purpose of illustration of a later stage of the method of use example illustrated in FIG. 11C.

Now referring to FIG. 11D, the conclusion of the thawing process described in FIGS. 11A through 11C is shown. At this stage of the thawing process, the upper heater block 1150 remains de-energized and in contact with the top flat surface of the upper shell part 1105. The solid contents 1115 in the vessel interior has completed phase change and the resulting liquid phase and has been displaced to the space above 1175 the driver card 1040 that is now biased to the inner surface of the lower flat vessel part 1110 by the magnet 1160. At or before this time in the thawing process, the heater block 1155 has been de-energized and no longer transfers heat into the vessel interior. In some embodiments, heater block 1155 and/or heater block 1150 may be actively chilled to maintain a desired working temperature for the liquid contents of the vessel following the thawing process.

Figure 12:
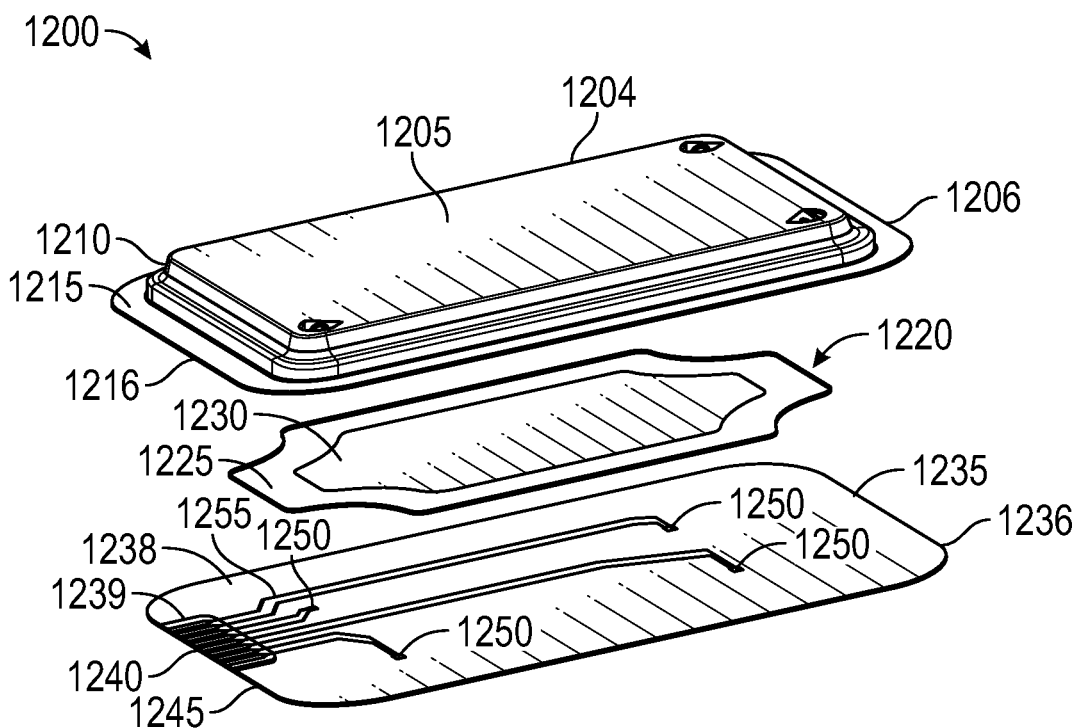
FIG. 12 shows an exploded view depicting the key elements of an embodiment of the invention comprising a solidified vessel contents bias driver card, and sensor circuitry embedded in a second vessel shell part, in accordance with a representative embodiment of the present invention.

Now referring to FIG. 12, an exploded view of an embodiment of the invention is shown wherein a first or upper vessel shell part 1204 comprising a planar surface 1205 joined to a swept rim 1210 at the perimeter edge, said swept rim 1210 further being joined at the opposite edge with a flange 1215 that occupies a plane that is parallel to the flat surface 1205, and is offset from the surface 1205. When assembled, the flange 1215 mates with and is heat welded to the matching region of a second or lower planar shell piece 1235 forming a containment vessel that completely isolates the interior volume from the environment. In some embodiments, a driver card 1220, comprising a ferritic sheet material 1230 that is laminated between two layers of material 1225 such that the ferritic sheet material 1230 is completely surrounded by the material 1225, and is thereby isolated in a watertight encasement, is enclosed within the vessel formed when the upper shell part 1204 is bonded to the lower shell part 1235. In some embodiments, the lower shell part 1235 is greater in length than the upper shell part 1204 so that when the upper shell part 1204 is bonded to the lower shell part 1235 with the edges 1206 and 1236 in a coincident orientation, the opposite end of the vessel shell part 1245 overhangs and extends beyond the upper vessel shell edge 1216. In some embodiments, the lower shell part 1235 comprises two heat bonded laminations of material. In some embodiments, the two lamination layers 1235 comprise sensors 1250 interposed between the laminations and connected by conductive material traces 1255 that terminate on the extended edge 1240 of the lower shell part 1235. In some embodiments, the sensors 1250 are temperature sensor. In some embodiments, the sensors 1250 are thermistors, RTD sensors, or thermocouple sensors. In some embodiments, the sensors communicate with the vessel interior or with the contents of the vessel directly through an area where the interior lamination is absent, while in other embodiments a material other than the vessel shell material is interposed between the sensor and the vessel interior or the vessel contents. In some embodiments, a portion of the top lamination layer 1238 is cut out 1239 exposing the termination of the conductive sensor traces 1240. In some embodiments, the conductive sensor traces may interface with complimentary electrical sockets whereby electronic data signals from the sensors 1250 may be conveyed to data processing circuitry. In some embodiment, the upper layer 1238 of the lower shell part 1235 is thinner than the second layer so that the temperature registered by the sensors 1250 closely correlates with the top surface of the upper layer 1238, and therefore with the temperature of the liquid contents contained within the vessel.

Figure 13A:
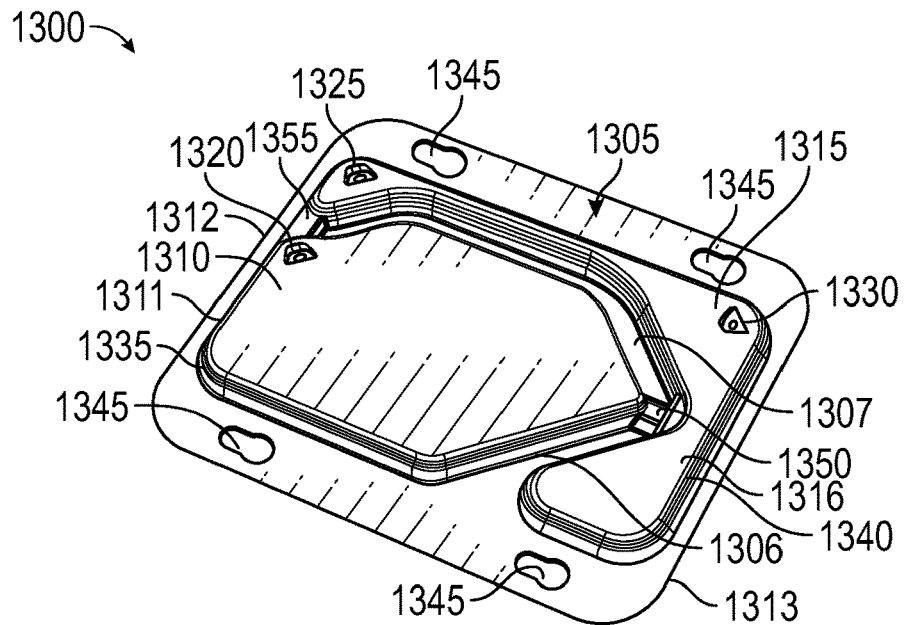
FIG. 13A shows a perspective view of an embodiment of the vessel wherein the vessel has been divided into two specific chambers that are connected by valves which are activated by acceleration forces, in accordance with a representative embodiment of the present invention.

Now referring to FIG. 13A, an embodiment of the invention is shown wherein the vessel 1300 comprises an upper shell part that further comprises two planar surfaces, a first planar surface 1310 being contiguous with a swept rim structure 1335 that forms a side of the upper shell part first chamber 1311, and a second planar surface 1315 being contiguous with a swept rim structure 1340 that forms a side of the upper shell part second chamber 1316, both swept rim structures 1335 and 1340 being contiguous with a rim flange 1305 that surrounds the perimeter of both chambers 1311 and 1316, and is contiguous with a flange 1306 that partially divides the two chambers, and both swept rim structures 1335 and 1340 being contiguous with a rim flange 1307 that further divides the two chambers 1311 and 1316. In some embodiments, the two chambers 1311 and 1316 are joined by a gas valve 1355 and a valve gate 1350 both of which are normally closed and both of which will open when subjected to a centrifugal force aligned with a specific centrifugal force field vector running perpendicular to the proximal edge 1312 of the flange rim 1305 to the distal edge 1313 of the flange rim 1305. Some embodiments comprise a loading port 1320 located within the planar surface 1310 of the first chamber 1311. Some embodiments comprise a loading port 1325 located within the planar surface 1315 of the second chamber 1316. In some embodiments, and extraction port 1330 is located within the planar surface 1315 of the second chamber 1316. In some embodiments, an additional vent port may be located within the planar surface 1315 of the second chamber 1316. In some embodiments, the flange rim 1305 may comprise two or more through-hole or keyhole cutout regions 1345.

Figure 13B:
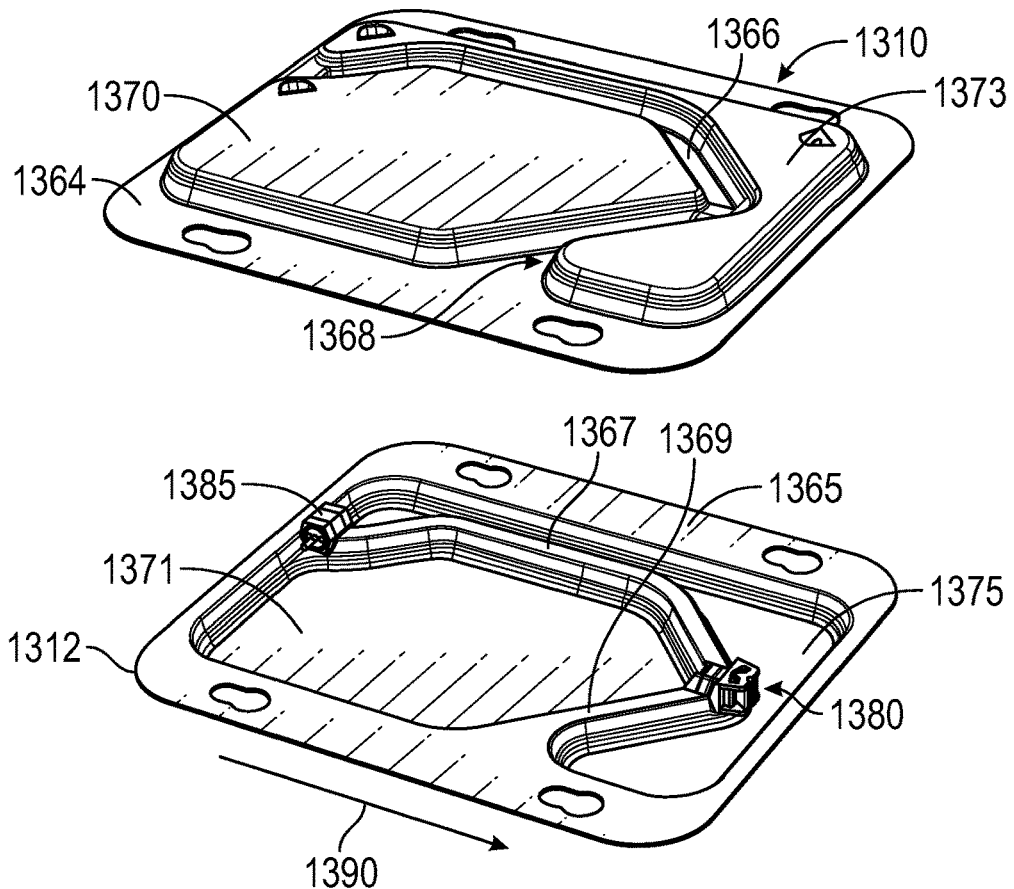
FIG. 13B shows an exploded view of the vessel shown in FIG. 13A, revealing the internal chamber and valve structures, in accordance with a representative embodiment of the present invention.

Now referring to FIG. 13B, an exploded view of the vessel embodiment described in FIG. 13A is shown. In some embodiments, an upper shell part 1310 comprising a perimeter flange 1364 that is contiguous with a planar surface 1368, and a second lower shell part 1312 comprising a perimeter flange 1365 that is contiguous with a planar surface 1369 mate in a heat weld that seals the perimeter of the vessel and partially divides the two chambers formed by the first chamber volume 1370 of the first shell part 1310 and the first chamber volume 1371 of the second lower shell part 1312, and the second chamber volume 1373 of the first shell part 1310 and the second chamber volume 1375 of the second lower shell part 1312. In some embodiments, a second surface 1366 of the first upper shell part 1310 and a second surface 1367 of the second lower shell part 1312 are joined in a heat weld to additionally and partially divide the first chamber volume (1371 and 1370) from the second chamber volume (1375 and 1373) such that the first and second chambers of the resulting vessel are separated except where connected by the gas valve 1385 and the gate valve 1380.

Figure 14A:
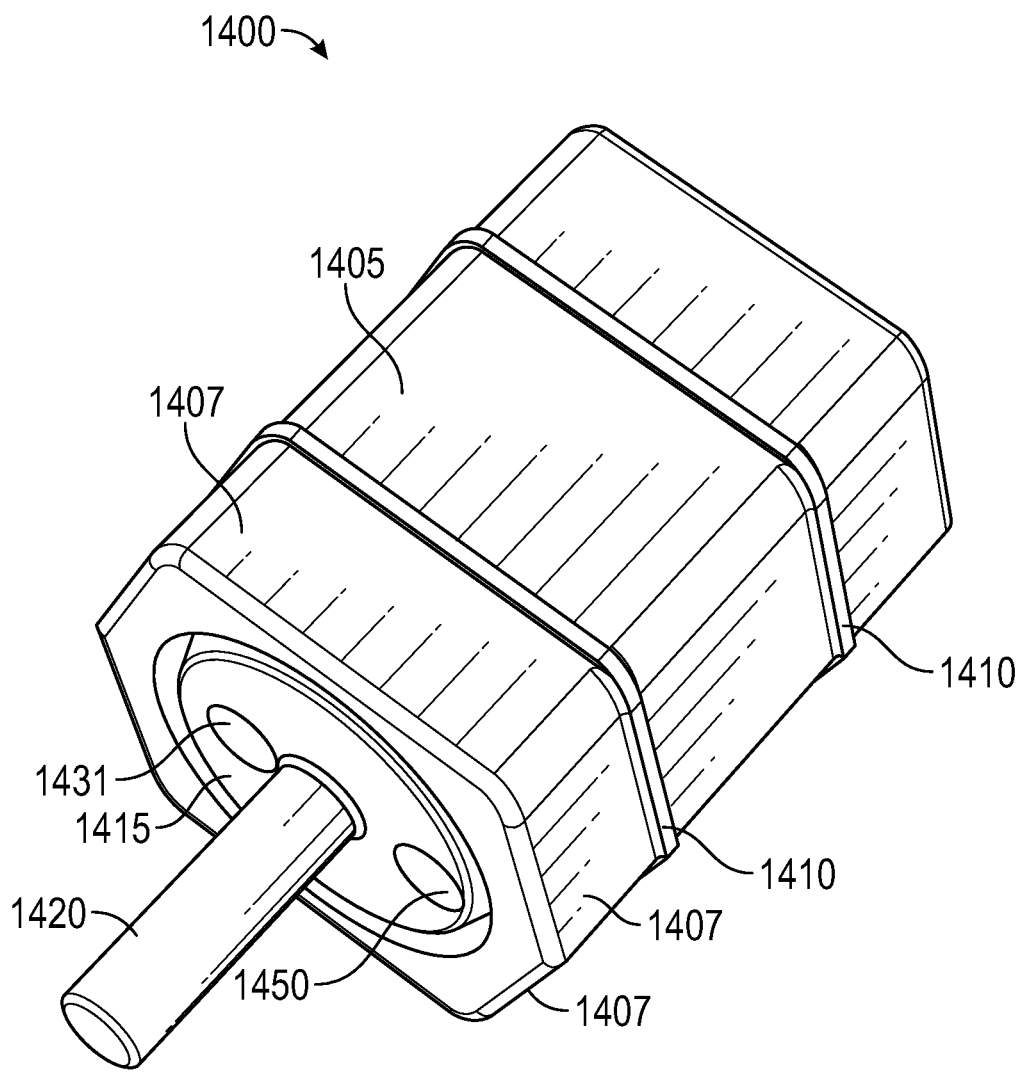
FIG. 14A shows a detailed view of a gas valve sub-component that is actuated by centrifugal forces, in accordance with a representative embodiment of the present invention.

Now referring to FIG. 14A, an example embodiment of a gas valve that may be used with some of the embodiments described in FIGS. 13A and 13B, is shown. In some embodiments, the valve housing 1405 of the gas valve 1400 comprised six external planar surfaces 1407 that, in some embodiments, are heat welded to counterpart internal surfaces in the vessel in which the gas valve may be installed. In some embodiments, valve housing 1405 comprises raised rib structures 1410 that may provide added material to fill welds between the surfaces 1407 and the counterpart internal surfaces of the vessel in which the gas valve may be installed. In some embodiments, a septum structure 1415 is held within the valve housing 1405. In some embodiments, the septum structure 1415 is monolithic molded part. In some embodiments, the septum part 1415 comprises a rubber material. In some embodiment the septum structure 1415 comprises a silicone rubber material. In some embodiments, the septum structure 1415 comprises an assembly handle 1420 to facilitate the insertion of the septum structure into the valve housing 1405. In some embodiments, the septum structure comprises a pressure equalization port 1450, and a gas passage port 1431, both described in greater detail in subsequent figures.

Figure 14B:
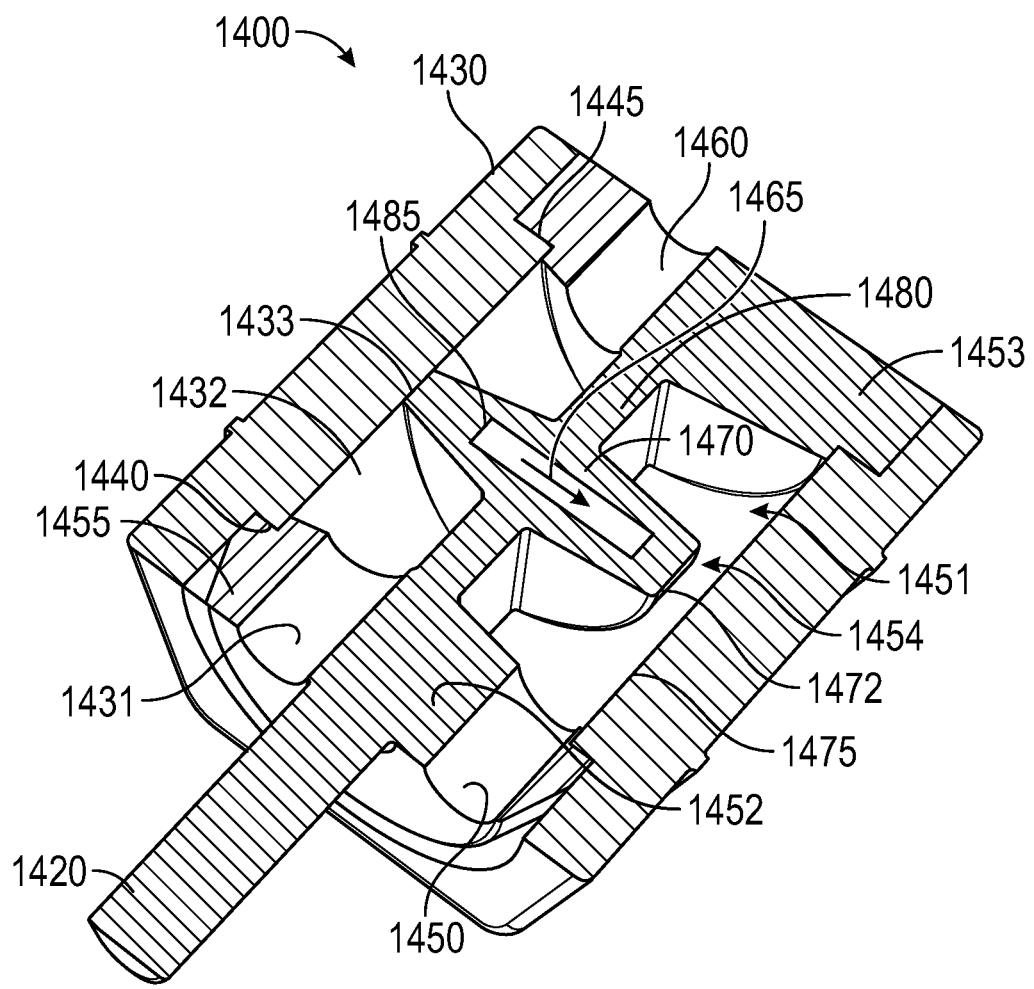
FIG. 14B shows a cross-section view of the gas valve shown in FIG. 14A.

Now referring to FIG. 14B, the gas valve described in FIG. 14A is shown in cross-section. In some embodiments, a valve housing 1430 with hexagonal outer surfaces contains a flexible rubber septum structure 1452. The septum structure 1452 comprises a first wall 1455 that communicates with the first chamber of the vessel (1371 and 1370 of FIG. 13B) and a second wall 1453 that communicates with the second chamber of the vessel (1375 and 1373 of FIG. 13B). The first wall 1455, in some embodiments, comprises a pressure equalization port 1450 which holds the pressure inside the non-sealing chamber 1451 of the valve at the same pressure as that of the first chamber of the vessel. The first wall 1455, in some embodiments, also comprises a passage port 1431 that is continuous with the valve chamber 1432. In some embodiments, the first wall 1455 seats within the valve housing and forms an annular seal at the interface 1440. The second wall 1453, in some embodiments, comprises a passage port 1460 that is continuous with the valve chamber 1432. In some embodiments, the second wall 1453 seats within the valve housing and forms an annular seal at the interface 1445. In some embodiments, the valve chamber 1432 is bisected and blocked by the valve gate 1470. In some embodiments, when a centrifugal force is applied along the vector 1465, the valve gate 1470 be displaced along the same vector 1465 and will flex the adjoining chamber membrane 1480 such that a gap will form between the valve gate 1470 and the valve housing 1430 at the junction 1433. In some embodiments, a dense material 1485 may be embedded in the valve gate 1470 to adjust the response of the valve to centrifugal force values. In some embodiments, the distance 1454 between the valve gate distal face 1472 and the valve housing interior face 1475 may be adjusted to limit of travel of the valve gate 1470 when displaced under centrifugal force load. In some embodiments, the septum structure 1452 comprises a rubber material. In some embodiments, the rubber material is a silicone rubber. In some embodiments, an assembly handle 1420 is molded into the septum structure 1452 to facilitate insertion and seating of the septum structure inside the valve housing 1430.

Figure 15A:
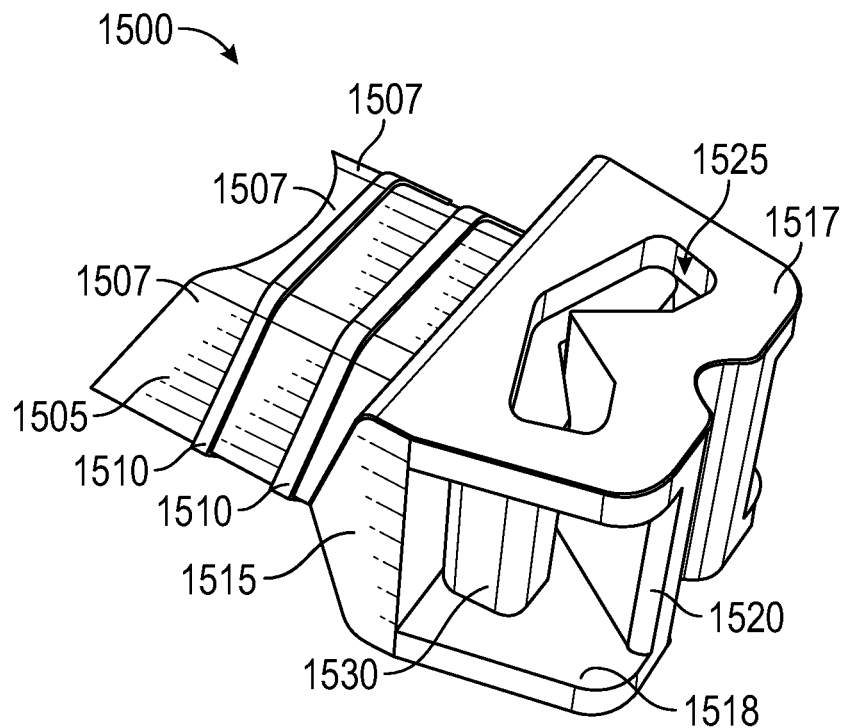
FIG. 15A shows a detailed view of a cell gate valve that is actuated by centrifugal forces, in accordance with a representative embodiment of the present invention.

Now referring to FIG. 15A, an example embodiment of a gate valve that may be used with some of the embodiments described in FIGS. 13A and 13B, is shown. In some embodiments, the valve housing 1505 of the gate valve 1500 comprised six external planar surfaces 1507 that, in some embodiments, are heat welded to counterpart internal surfaces in the vessel in which the gas valve may be installed. In some embodiments, gate valve housing 1505 comprises raised rib structures 1510 that may provide added material to fill welds between the surfaces 1507 and the counterpart internal surfaces of the vessel in which the gas valve may be installed. In some embodiments, the gate valve comprises a gate housing valve seat 1515 that, in some embodiments, is joined to a V-block structure 1520 through two connector plates 1517 and 1518. In some embodiments, a flexible gate 1530 is held within the structure formed by the valve seat 1515, the connector plates 1517 and 1518, and the V-block structure 1520. In some embodiments, the upper connector plate 1517 comprises an opening 1525 through which the flexible gate 1530 may be inserted into the valve structure.

Figure 15B:
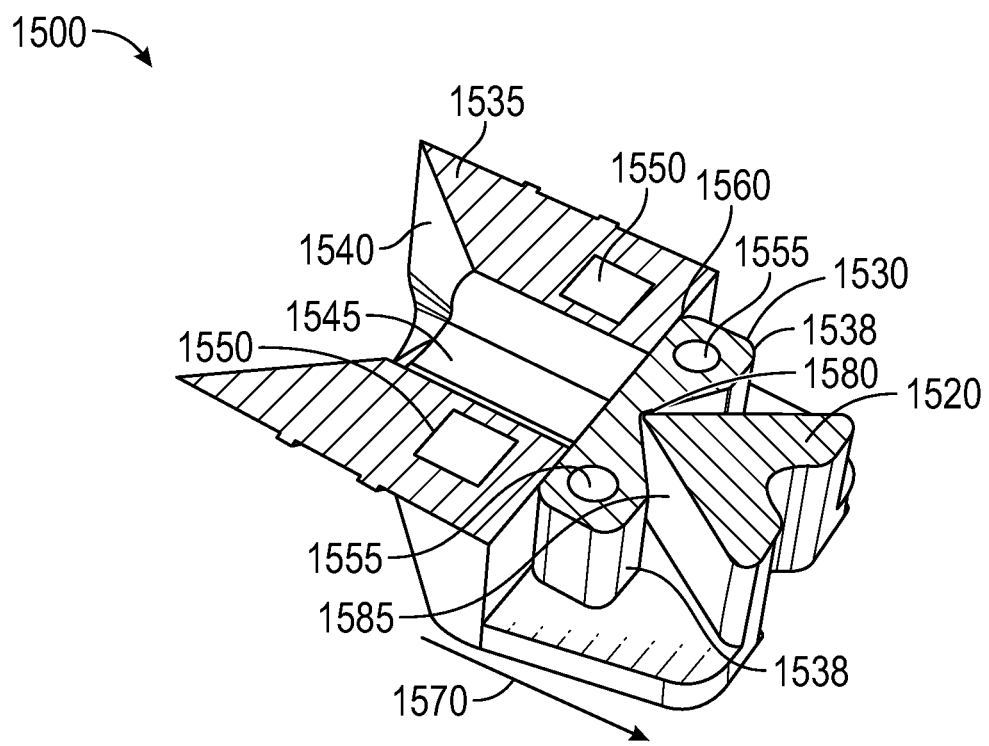
FIG. 15B shows a cross-section view of the cell gate valve shown in FIG. 15A.

Now referring to FIG. 15B, a cross-section view of the gate valve 1500 described in FIG. 15A is shown. Now visible in the cross-section is the communication tunnel 1545 that, in some embodiments, connects the first chamber opening 1540 and the second chamber opening at the valve seat 1560. In some embodiments, permanent magnets 1550 flanking both sides of the communication tunnel 1545 may be embedded into the valve housing 1535. In some embodiments, a flexible gate 1530 is interposed between the valve seat 1560 and the leading edge 1580 of the V-block structure 1520. In some embodiments, the flexible gate 1530 comprises two ferritic pieces 1555 that may be attracted by the permanent magnets 1550, thereby holding the closure sides 1538 of the flexible gate 1530 in contact with the valve seat 1560, thereby closing off the communication tunnel 1545. In some embodiments, when a centrifugal force aligned with the vector 1570 is applied to the flexible gate 1530, the closure sides 1538 are displaced toward the V-block and are unseated from the valve seat 1560, thereby allowing passage through from the first chamber side 1540 of the communication tunnel 1545 to the valve seat 1560 side of the communication tunnel. In some embodiments, as the value of the centrifugal force aligned with the vector 1570 is returned to zero, the magnetic attraction of the magnets 1550 upon the ferritic pieces 1555 returns the closure sides 1538 of the valve gate 1530 to once again to settle on the valve seat 1560 and close off the communication tunnel 1545. In some embodiments, all metallic and magnetic materials are isolated from direct contact with fluids that may flow through or accumulate around the any parts of the gate valve 1500. While the described embodiment has been described as comprising a detailed and specific example of a gas valve and a gate valve, it may be appreciated by one familiar with the art that numerous valve designs may serve the same function and therefore the example provided is not intended to be limiting or exclusive to the valve design shown or to the means by which the valve is actuated. For example in some embodiments, one or more valves may be actuated by a magnetic field, while in other embodiments one or more valves may be actuated by an electrical field.

Figure 16A:
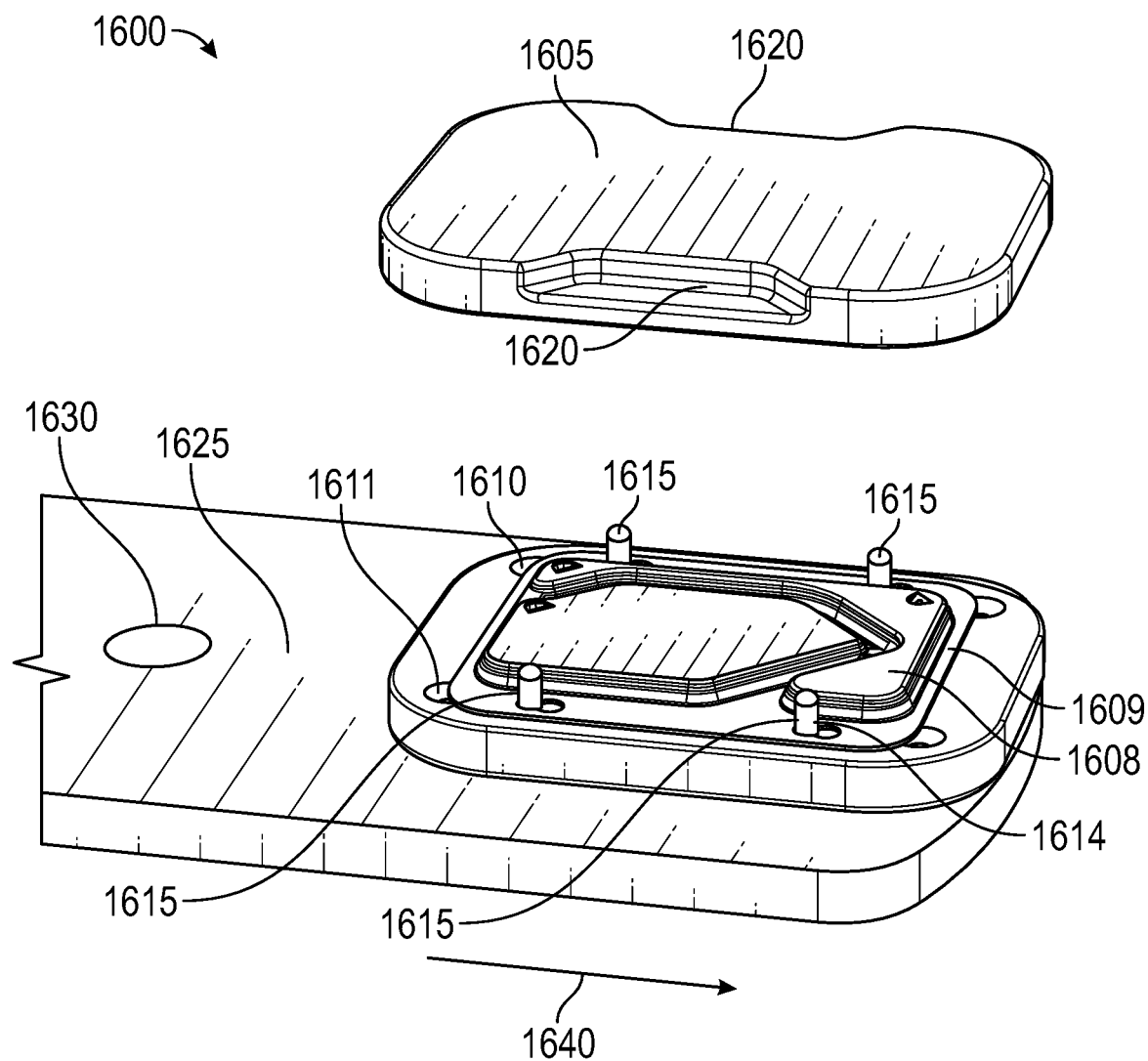
FIG. 16A, is a perspective view of a partially assembled shell storage vessel coupled to a representative centrifuge machinery for the purpose of applying a centrifugal force to the embodiment, in accordance with a representative embodiment and method of the present invention.

Now referring to FIG. 16A, a vessel embodiment 1608 (shown and described in FIGS. 13A and 13B as vessel 1300) is shown mounted in the second half of a retainer 1610 that comprises a cavity (shown in FIG. 16B, below) configured to receive and contact the exterior of the vessel 1608 at the major planar surface (occluded) and along the vessel rim 1609. The four keyhole slots 1614 of the vessel 1608 fit over four pin counterparts 1615 that are affixed in the retainer 1610, and thereby prevent a displacement of the vessel embodiment along the radial force vector 1640. In some embodiments, the lower retainer part 1610 is affixed to the centrifuge arm 1625 by a one or more fasteners 1611, such as threaded bolts or screws. The vessel may further be fully enclosed by affixing four holes (obscured) of an upper retainer 1605 over the corresponding pins 1615, and which may be subsequently clamped to the centrifuge arm 1625 at the two lateral recess surfaces 1620. Upon rotation of the centrifuge arm 1625 on the axle 1630, a centrifugal force is imposed on the vessel 1608 and the contents therein.

Figure 16B:
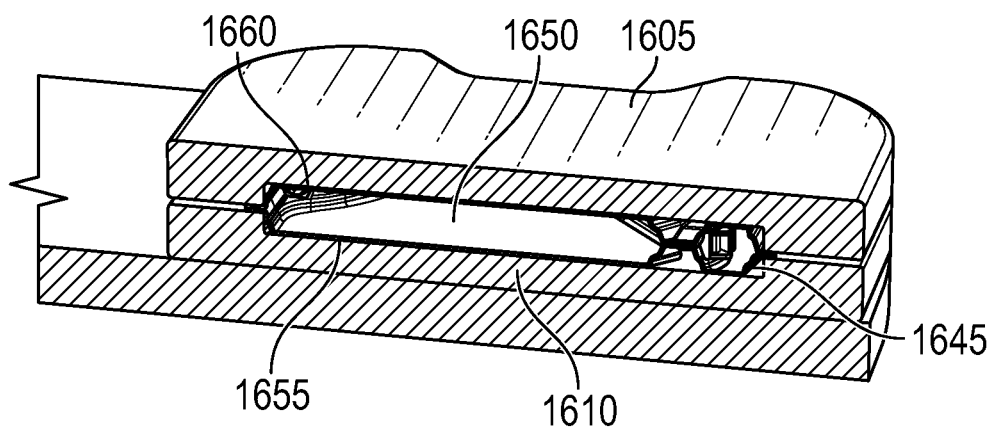
FIG. 16B shows a cross-section view of the fully assembled and installed shell storage vessel of FIG. 16A, further illustrating the vessel shape-restraining features of the centrifuge machinery, in accordance with a representative embodiment of the present invention.

Now referring to FIG. 16B, a cross-section is shown of the assembly of FIG. 16A. In some embodiments, the vessel 1645 closely mates on the outer surface of the upper vessel shell part 1660 and the outer surface of the lower vessel shell part 1655 with the internal cavity surface counterparts of the upper retainer 1605 and the lower retainer 1610 respectively. In some embodiments, the vessel 1645 is subjected to a centrifugal force, the vessel fluid contents will impose an outward hydrostatic pressure on the upper vessel shell part 1660 and the lower vessel shell part 1655 and may distort and stress the vessel but for the restraining influence of the upper retainer 1605 and the lower retainer 1610.

Figure 16C:
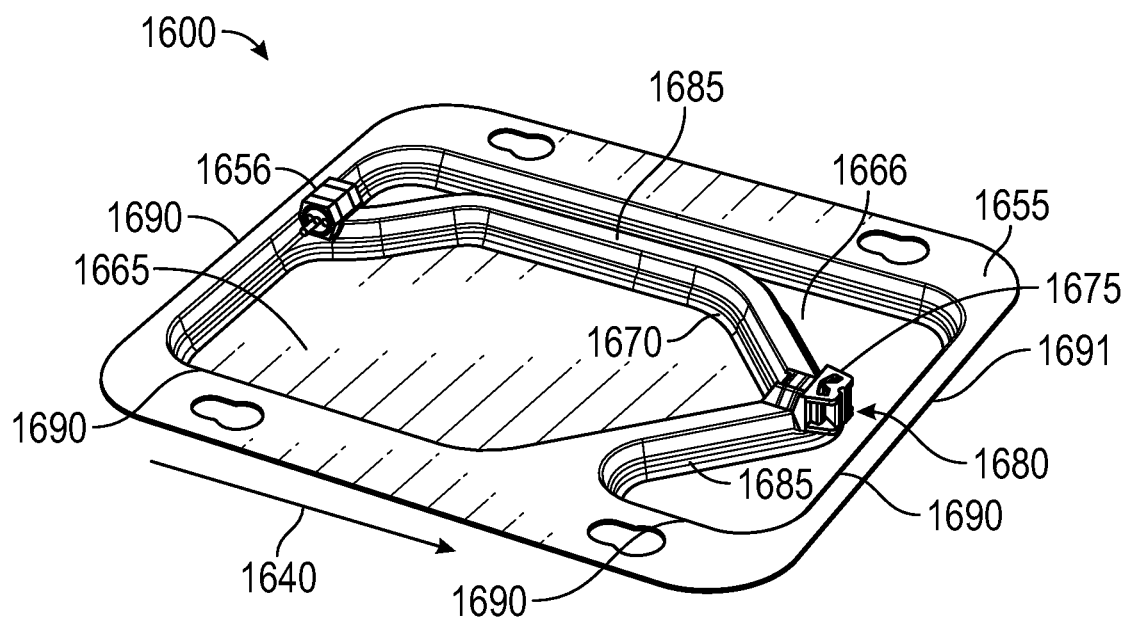
FIG. 16C shows a perspective top view the second lower shell part of the shell storage vessel shown in FIGS. 13A and 13B.

Now referring to FIG. 16C, a the vessel embodiment described in FIGS. 16A and 16B is shown with the upper shell part removed. In some embodiments, the lower vessel shell part 1655 comprises a first chamber 1665 and a second chamber 1666 that are partially isolated by a middle wall 1685 that separates the two chambers along a path. The wall separation 1685 is interrupted by the centrifugal force actuated valve gate 1675 and the centrifugal force actuated gas valve 1656. In some methods, a procedure by which an exchange of the fluid in which a number of cells are suspended and contained within the first chamber 1665 may be conducted prior to recovery of the cells from the vessel. In some methods, the first chamber 1665 of the vessel is occupied by a cell suspension containing a cryoprotectant fluid and a small volumetric proportion of gas, and the second chamber 1666 is occupied by an exchange fluid and a small volumetric proportion of gas. In some embodiments, the proportional volumes of the fluids in the two chambers are adjusted such that when the vessel is subjected to a centrifugal force along vector 1640 and the contents of both chambers 1665 and 1666 are biased to the distal side 1691 of the vessel, a hydrostatic pressure differential across the valve gate 1675 is minimized. In some methods, the density of the fluid in the second chamber 1666 is equal to or somewhat greater than the density of the fluid in the first chamber 1665. In some methods, the cells within the first chamber 1665 migrate to the second chamber 1666 via the passage tunnel (obscured) of the gate valve 1675 when vessel 1600 is subjected to centrifugal force along vector 1640. In some methods, when a sufficient centrifugal force is applied, the gas valve 1656 open and allow an equilibration of gas pressures between the two chambers 1665 and 1666. In some methods, when a sufficient centrifugal force is applied, valve gate 1675 opens and allows the cells in first chamber 1665 to migrate through valve gate 1675 and into the second chamber 1666. In some methods, a hydrostatic equilibrium between the fluids in the two chambers 1665 and 1666 is achieved, thereby negating any hydrostatic pressure induce displacement of the boundary between the two fluids. In some methods, when a predetermined amount of time has elapsed and/or it is otherwise determined that the cells within the first chamber 1665 have completely migrated into the second chamber 1666, the angular velocity of the centrifuge is reduced to zero, during which interval the gas valve 1656 and the gate valve 1675 resume a closed position, thereby again isolating the two chambers. Following centrifugation of vessel 1600, in some embodiments vessel 1600 is removed from the centrifuge and chamber 1666 is vented at the filling port (not shown), whereby the cell suspension in the second chamber 1666 is recovered through the extraction port (not shown).

The foregoing discussion of the invention has been presented for purposes of illustration and description. The foregoing in not intended to limit the invention to the form or forms disclosed herein. Although the description of the invention has included description of one embodiment and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those disclosed herein, and without intending to publicly dedicate any patentable subject matter.

The invention claimed is:

1. A vessel comprising:
   a first shell part having a first dimension, a second dimension and a third dimension, the first and second dimensions of the first shell part defining a first major surface area, the first major surface area comprising rounded corners, and a perimeter of the first shell part having a first swept rim profile extending therefrom and a first flange that is parallel to the first major surface area, connected to and extending outwardly from an edge of the first swept rim profile of the perimeter of the first shell part, wherein the third dimension of the first shell defines a distance from a first major surface of the first major surface area to the first flange;
   a second shell part having a first dimension, a second dimension and a third dimension, the first and second dimensions of the second shell part defining a second major surface area, the second major surface area comprising rounded corners, and a perimeter of the second shell part having a second swept rim profile extending therefrom and a second flange that is parallel to the second major surface area, connected to and extending outwardly from an edge of the second swept rim profile of the perimeter of the second shell part, wherein the third dimension of the second shell defines a distance from a second major surface of the second major surface area to the second flange; and
   an enclosed volume defined by a space interposed between an inner surface of the first shell part and an inner surface of the second shell part when a face surface of the first flange is joined together with a face surface of the second flange, wherein the enclosed volume is isolated from an exterior of the vessel;
   wherein the first swept rim profile comprises a changeable curvature having a length extendable to permit an increase or contractable to permit a decrease in a distance between the first major surface area of the first shell part and the second major surface area of the second shell part, such that the enclosed volume is increased or decreased, while allowing the first and second major surface areas to remain planar through the increase or decrease.

2. The vessel of claim 1, wherein the vessel is comprised of a thermoplastic material.

3. The vessel of claim 1, wherein the face surfaces of the first and second flanges are joined by a heat weld.

4. The vessel of claim 2, wherein the thermoplastic material is a copolyester.

5. The vessel of claim 1, further comprising a depression formed in at least one of the first and second major surfaces.

6. The vessel of claim 5, wherein the depression comprises a single radially symmetrical wall.

7. The vessel of claim 5, wherein the depression comprises at least two walls.

8. The vessel of claim 7, wherein the at least two walls comprise a subregion having a thickness less than a wall thickness of a remainder of the at least two walls.

9. The vessel of claim 5, wherein the depression is located on a corner surface of at least one of the first and second major surfaces.

10. The vessel of claim 5, further comprising a through-hole in communication with the enclosed volume and joined to a solid material part via a heat weld, wherein the solid material part selectively seals the through-hole to isolate the though-hole from the exterior of the vessel.

11. The vessel of claim 5, wherein the depression is located on at least one of the first swept rim profile and the second swept rim profile of the vessel.

12. The vessel of claim 5, further comprising an airtight label reversibly bonded to the exterior of the vessel and placed overtop the depression to isolate a volume of the depression from the exterior of the vessel.

13. The vessel of claim 1, wherein a ratio between the first dimension of the first shell part and a combined dimension of the second and third dimensions of the first shell part is from 1:1 to 4:1.

14. The vessel of claim 1, wherein a ratio between the first dimension of the first shell part and the third dimension of the first shell part is from 1:1 to 30:1.

15. The vessel of claim 1, wherein a ratio between the first dimension of the first shell part and third dimension of the first shell part is from 2:1 to 20:1.

16. The vessel of claim 1, wherein the first dimension of the first shell part multiplied by the second dimension of the first shell part is from 3 cm² to 300 cm².

17. The vessel of claim 1 wherein the first dimension of the first shell part multiplied by the second dimension of the first shell part is from 300 cm² to 1000 cm².

18. The vessel of claim 1, wherein at least one of the first and second flanges have a width greater than 1 mm.

19. The vessel of claim 1, further comprising a protective bumper in contact with a perimeter edge of the first and second flanges.

20. The vessel of claim 19, wherein the protective bumper encases a portion of the perimeter edge of the first and second flanges.

21. The vessel of claim 19, wherein the protective bumper is constructed from a felt material.

22. The vessel of claim 1, wherein the first shell part is a molded shell, the second shell part is a planar sheet, and the first and second shell parts are nominally rectangular.

23. The vessel of claim 1, further comprising a conduit forming a portion of at least one of the first and second swept rim profiles.

24. The vessel of claim 23, wherein a perimeter edge of the second flange of the second shell part extends beyond a perimeter edge of the first flange of the first shell part.

25. The vessel of claim 1, further comprising a cutout region provided in at least one of the first flange and the second flange.

26. The vessel of claim 1, further comprising at least one of an electrically conductive circuit and an electronic sensor interposed between a first lamination layer and a second lamination layer of the first or second shell part.

27. The vessel of claim 26, wherein the electronic sensor is a temperature sensor.

28. The vessel of claim 26, wherein a contact portion of the conductive circuit is exposed and/or accessible through the first or second lamination layer.

29. The vessel of claim 1, further comprising an element disposed within the enclosed volume.

30. The vessel of claim 29, wherein the element comprises a ferritic sheet material laminated between two sheets of inert material.

31. The vessel of claim 30, wherein the inert material comprises a polymer.

32. The vessel of claim 1, wherein the enclosed volume comprises a plurality of chambers.

33. The vessel of claim 32, wherein at least two of the plurality of chambers are independent from one another.

34. The vessel of claim 32, wherein at least one of the plurality of chambers comprises a liquid selected from the group consisting of a solution, a composition, a formulation, a particulate suspension, a viral suspension, a cellular suspension, and a multicellular organism suspension.

35. The vessel of claim 32, wherein at least two chambers of the plurality of chambers are interconnected.

36. The vessel of claim 35, wherein the at least two chambers are interconnected by a pathway selected from the group consisting of a passageway, a conduit, a valve, a gate, an aperture, a lumen, a tube, a channel, and a tunnel.

37. The vessel of claim 1, wherein at least one of the first and second shell parts are formed via a vacuum molding process.

38. A method for storing a liquid in a vessel including: a first shell part having a first dimension, a second dimension and a third dimension, the first and second dimensions of the first shell part defining a first major surface area, the first major surface area comprising rounded corners, and a perimeter of the first shell part having a first swept rim profile extending therefrom and a first flange that is parallel to the first major surface area, connected to and extending outwardly from an edge of the first swept rim profile of the perimeter of the first shell part, wherein the third dimension of the first shell defines a distance from a first major surface of the first major surface area to the first flange; a second shell part having a first dimension, a second dimension and a third dimension, the first and second dimensions of the second shell part defining a second major surface area, the second major surface area comprising rounded corners, and a perimeter of the second shell part having a second swept rim profile extending therefrom and a second flange that is parallel to the second major surface area, connected to and extending outwardly from an edge of the second swept rim profile of the perimeter of the second shell part, wherein the third dimension of the second shell defines a distance from a second major surface of the second major surface area to the second flange; an enclosed volume defined by a space interposed between an inner surface of the first shell part and an inner surface of the second shell part when a face surface of the first flange is joined together with a face surface of the second flange, wherein the first swept rim profile comprises a changeable curvature having a length extendable to permit an increase or contractable to permit a decrease in a distance between the first major surface area of the first shell part and the second major surface area of the second shell part, such that the enclosed volume is increased or decreased, while allowing the first and second major surface areas to remain planar through the increase or decrease, said method comprising:

locating a corner of the vessel, the corner having a depression;

elevating the corner to a position that is higher than any remaining corner of the vessel;

puncturing the depression;

accessing the enclosed volume of the vessel through the punctured depression;

inserting a filling needle into the punctured depression;

introducing a liquid into the enclosed volume via a first portion of the filling needle while simultaneously removing displaced gas from the enclosed volume via a second portion of the filling needle;

withdrawing the filling needle from the enclosed volume and punctured depression; and occluding the punctured depression.

39. The method of claim 38, further comprising applying a protective cover over the occluded punctured depression.

40. The method of claim 38, further comprising removing a protective cover from the depression prior to the step for puncturing the depression.

41. The method of claim 38, wherein occluding the punctured depression comprises inserting a plug into the punctured depression.

42. The method of claim 41, further comprising fusion sealing the plug to the depression, wherein the enclosed volume is isolated from an exterior of the vessel.

43. A method for withdrawing a liquid from a vessel containing the liquid, the vessel including: a first shell part having a first dimension, a second dimension and a third dimension, the first and second dimensions of the first shell part defining a first major surface area, the first major surface area comprising rounded corners, and a perimeter of the first shell part having a first swept rim profile extending therefrom and a first flange that is parallel to the first major surface area, connected to and extending outwardly from an edge of the first swept rim profile of the perimeter of the first shell part, wherein the third dimension of the first shell defines a distance from a first major surface of the first major surface area to the first flange; a second shell part having a first dimension, a second dimension and a third dimension, the first and second dimensions of the second shell part defining a second major surface area, the second major surface area comprising rounded corners, and a perimeter of the second shell part having a second swept rim profile extending therefrom and a second flange that is parallel to the second major surface area, connected to and extending outwardly from an edge of the second swept rim profile of the perimeter of the second shell part, wherein the third dimension of the second shell defines a distance from a second major surface of the second major surface area to the second flange; and an enclosed volume defined by a space interposed between an inner surface of the first shell part and an inner surface of the second shell part when a face surface of the first flange is joined together with a face surface of the second flange, wherein the first swept rim profile comprises a changeable curvature having a length extendable to permit an increase or contractable to permit a decrease in a distance between the first major surface area of the first shell part and the second major surface area of the second shell part, such that the enclosed volume is increased or decreased, while allowing the first and second major surface areas to remain planar through the increase or decrease, said method comprising:
    locating a first corner of the vessel, the first corner having a first depression;
    elevating the first corner to a position that is higher than any remaining corner of the vessel;
    puncturing the depression with a venting tool;
    locating a second depression on a second corner of the vessel that is positioned opposite the first corner of the vessel;
    puncturing the second depression with an extraction tool; and
    withdrawing the liquid from the vessel.

44. The method of claim 43, further comprising removing a protective cover from at least one of the first and second depressions prior to puncturing.

45. The method of claim 43, wherein the venting tool and extraction tool are sterile.

46. A method for thawing solidified contents of a vessel including a first shell part having a first dimension, a second dimension and a third dimension, the first and second dimensions of the first shell part defining a first major surface area, the first major surface area comprising rounded corners, and a perimeter of the first shell part having a first swept rim profile extending therefrom and a first flange that is parallel to the first major surface area, connected to and extending outwardly from an edge of the first swept rim profile of the perimeter of the first shell part, wherein the third dimension of the first shell defines a distance from first major surface of the first major surface area to the first flange; a second shell part having a first dimension, a second dimension and a third dimension, the first and second dimensions of the second shell part defining a second major surface area, the second major surface area comprising rounded corners, and a perimeter of the second shell part having a second swept rim profile extending therefrom and a second flange that is parallel to the second major surface area, connected to and extending outwardly from an edge of the second swept rim profile of the perimeter of the second shell part, wherein the third dimension of the second shell defines a distance from a second major surface to the second major surface area to the second flange; an enclosed volume defined by a space interposed between an inner surface of the first shell part and an inner surface of the second shell part when a face surface of the first flange is joined together with a face surface of the second flange; and including an element disposed within the enclosed volume, wherein the element is in contact with an interior surface of the first shell part that corresponds to the first major surface area, wherein the first swept rim profile comprises a changeable curvature having a length extendable to permit an increase or contractable to permit a decrease in a distance between the first major surface area of the first shell part and the second major surface area of the second shell part, such that the enclosed volume is increased or decreased, while allowing the first and second major surface areas to remain planar through the increase or decrease, the method comprising:
    clamping the vessel between a first heater block and a second heater block, wherein the first heater block is in contact with the first major surface area, and the second heater block is in contact with the second major surface area, the second heater block further comprising a magnetic source;
    increasing a temperature of the first and second heater blocks;
    activating the magnetic source;
    magnetically attracting the element to an interior surface of the second shell part that corresponds to the second major surface area; and
    biasing the solidified contents against the interior surface of the second shell part via the element and the magnetic source.

47. The method of claim 46, further comprising decreasing a temperature of the first heater block at a time in which a liquid phase of the solidified contents is present within the vessel.

48. The method of claim 46, further comprising removing the first and second heater blocks from the vessel.

49. A method for transferring cells from a cryoprotectant media to a recovery media using a vessel including a first shell part having first dimension, a second dimension and a third dimension, the first and second dimensions of the first shell part defining a first major surface area, the first major surface area comprising rounded corners, and a perimeter of the first shell part having a first swept rim profile extending therefrom and a first flange that is parallel to the first major surface area, connected to and extending outwardly from an edge of the first swept rim profile of the perimeter of the first shell part, wherein the third dimension of the first shell defines a distance from a first major surface of the first major surface area to the first flange; a second shell part having a first dimension, a second dimension and a third dimension, the first and second dimensions of the second shell part defining a second major surface area, the second major surface area comprising rounded corners, and a perimeter of the second shell part having a second swept rim profile extending therefrom and a second flange that is parallel to the second major surface area, connected to and extending outwardly from an edge of the second swept rim profile of the perimeter of the second shell part, wherein the third dimension of the second shell defines a distance from a second major surface of the second major surface area to the second flange; an enclosed volume defined by a space interposed between an inner surface of the first shell part and an inner surface of the second shell part when a face surface of the first flange is joined together with a face surface of the second flange, wherein the enclosed volume comprises a plurality of chambers; wherein the first swept rim profile comprises a changeable curvature having a length extendable to permit an increase or contractable to permit a decrease in a distance between the first major surface area of the first shell part and the second major surface area of the second shell part, such that the enclosed volume is increased or decreased, while allowing the first and second major surface areas to remain planar through the increase or decrease, said method comprising:
- filling a first chamber of the vessel with a cell suspension;
- filling a second chamber of the vessel with a media selected from the group consisting of a recovery media and an injection media;
- interconnecting the first and second chambers by a first pathway having a gate comprising a closed state and an open state, wherein the closed state is changed to the open state by subjecting the vessel to a centrifugal force;
- interconnecting the first and second chambers by a second pathway comprising a valve configured to permit passage of gas in response to the centrifugal force; and
- subjecting the vessel to the centrifugal force, whereupon the cell suspension from the first chamber passes into the second chamber via the gate, and gas within the second chamber passes into the first chamber via the valve.

50. The method of claim 49, wherein the second pathway is positioned distal to the first chamber along a centrifugal force field vector of the vessel.

51. The method of claim 49, wherein a portion of the second chamber is positioned distal to the gate and along a centrifugal force field vector of the vessel.

52. The method of claim 49, further comprising positioning a gas within the second chamber to a proximal end of the second chamber that runs parallel to the first chamber and connects the first chamber to the first chamber via the valve, such that only the media within the second chamber contacts the gate.

53. The method of claim 49, wherein the centrifugal force simultaneously promotes the cell suspension to pass through the gate and into the second chamber, and gas to pass from the second chamber and into the first chamber via the valve.

54. The method of claim 49, further comprising resuming the closed state of the gate and closing the valve by reducing the centrifugal force.

55. The method of claim 54, further comprising gently agitating the cell suspension and the media in the second chamber.

56. The method of claim 55, further comprising removing the cell suspension and media from the second chamber via an extraction port of the vessel.

57. The vessel of claim 1, wherein the changeable curvature is a double back curvature or S-shaped.

* * * * *